US008541175B2

(12) United States Patent
Wehrman et al.

(10) Patent No.: US 8,541,175 B2
(45) Date of Patent: *Sep. 24, 2013

(54) DETECTION OF MOLECULAR INTERACTIONS USING A REDUCED AFFINITY ENZYME COMPLEMENTATION REPORTER SYSTEM

(75) Inventors: Tom Wehrman, Fremont, CA (US); Helen M. Blau, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 11/717,579

(22) Filed: Mar. 12, 2007

(65) Prior Publication Data

US 2007/0275397 A1 Nov. 29, 2007

Related U.S. Application Data

(60) Provisional application No. 60/782,054, filed on Mar. 13, 2006.

(51) Int. Cl.
*G01N 33/53* (2006.01)
*C12N 9/14* (2006.01)

(52) U.S. Cl.
USPC .......................................... 435/7.1; 435/195

(58) Field of Classification Search
None
See application file for complete search history.

(56) References Cited

U.S. PATENT DOCUMENTS

| 4,378,428 | A | 3/1983 | Farina |
| 4,708,929 | A | 11/1987 | Henderson |
| 5,037,735 | A | 8/1991 | Khanna |
| 5,106,950 | A | 4/1992 | Farina |
| 5,362,625 | A | 11/1994 | Krevolin |
| 5,464,747 | A | 11/1995 | Eisenbeis |
| 5,604,091 | A | 2/1997 | Henderson |
| 5,643,734 | A | 7/1997 | Henderson |
| 2003/0219848 | A1 | 11/2003 | Naqvi |

FOREIGN PATENT DOCUMENTS

| EP | 1466624 A1 | 10/2004 |
| WO | WO9203559 A2 | 3/1992 |
| WO | WO9619732 A1 | 6/1996 |
| WO | WO9806648 A1 | 2/1998 |
| WO | WO0039348 A1 | 7/2000 |
| WO | WO0100214 A1 | 1/2001 |
| WO | WO0160840 A2 | 8/2001 |
| WO | 2005113838 A2 | 12/2005 |

OTHER PUBLICATIONS

Richards et al., Cell. Mol. Life Scie., 53:790-802, 1997.*
Mohler, William A. et al., "Gene expression and cell fusion analyzed by lacZ complementation in mammalian cells," Proc. Natl. Acad. Sci. USA, Oct. 1996, vol. 93, 12423-12427.
Rossi, Fabio et al., "Monitoring protein-protein interactions in intact eukaryotic cells by Beta-galactosidase complementation," Proc. Natl. Acad. Sci. USA, Aug. 1997, vol. 94, 8405-8410.
Blakely, Bruce T. et al., "Epidermal growth factor receptor dimerization monitored in live cells," Nature Biotechnology, Feb. 2000, vol. 18, 218.
Wehrman, Thomas et al., "Protein-protein interactions monitored in mammalian cells via complementation of Beta-lactamase enzyme fragments," PNAS, Mar. 19, 2002, vol. 99, No. 6, 3469-3474.
Eglen, Richard M. et al., "Beta Galactosidase Enzyme Fragment Complementation as A Novel Technology for High Throughput Screening," Combinatorial Chemistry & High Throughput Screening, 2003, vol. 6, 381-387.
Extended European Search Report, Sep. 10, 2009.
Abbas-Terki, et al., Eur. J. Biochem. "Alpha-complemented beta-galactosidase. An in vivo model substrate for the molecular chaperone heat-shock protein 90 in yeast", 1999, 266(2):517-23.
Douglas, et al., Proc. Natl. Acad. Sci. USA, "Intracellular targeting and import of an F1-ATPase beta-subunit-beta-galactosidase hybrid protein into yeast mitochondria", 1984, 81(13):3983-7.
Homma, et al., Biochem. Biophys. Res. Commun., "Intracellular stability of alpha fragments of beta-galactosidase: effects of amino-terminally fused polypeptides", 1995, 215(2):452-8.
Miller, et al., Gene, "A quantitative beta-galactosidase alpha-complementation assay for fusion proteins containing human insulin B-chain peptides", 1984, 29:247-50.
Thomas and Kunkel, Proc. Natl. Acad. Sci. USA, "Replication of UV-irradiated DNA in human cell extracts: evidence for mutagenic bypass of pyrimidine dimers", 1993, 90:7744-8.
Wehrman et al., Nat. Methods, "Enzymatic detection of protein translocation", 2005, 2:521-7.
Keith E. Langley, et al., Molecular basis of beta-Galactosidease alpha-Complementation, Proc. Nat. Acad. Sci. USA, Vold 72, No. 4, pp. 1254-1257, Apr. 1975.
English Translation of Office Action issued Jan. 19, 2011 in Chinese application 200780017417.7.
Yan, et al., "Cell-based high-throughput screening assay system for monitoring G protein-coupled receptor activation using beta-Galactosidase enzyme complementation technology", Journal of Biomolecular Screening, vol. 7, No. 5, 2002, pp. 451-459.
EP Office Action Search Report, Application No. 07752920.4, Aug. 2, 2011, 8 pp.

* cited by examiner

*Primary Examiner* — Nancy T Vogel
(74) *Attorney, Agent, or Firm* — David J. Aston; Peters Verny, LLP

(57) ABSTRACT

Methods and compositions for detecting molecular interactions are provided. Aspects of the invention include the use of a reduced affinity enzyme complementation reporter system. Also provided are systems and kits for use in practicing embodiments of the methods.

13 Claims, 7 Drawing Sheets

SEQUENCE LISTING

<160> NUMBER OF SEQ ID NOS: 7

<210> SEQ ID NO 1
<211> LENGTH: 52
<212> TYPE: PRT
<213> ORGANISM: E.coli

<400> SEQUENCE: 1

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala Arg Pro
            20                  25                  30

Pro Phe Ala Ser Trp Arg Asn Ser Glu Glu Ala Arg Thr Asp Arg Pro
        35                  40                  45

Ser Gln Gln Leu

<210> SEQ ID NO 2
<211> LENGTH: 52
<212> TYPE: PRT
<213> ORGANISM: E.coli

<400> SEQUENCE: 2

Met Gly Val Ile Thr Asp Ser Leu Ala Val Val Leu Gln Arg Arg Asp
1               5                   10                  15

Trp Glu Asn Pro Gly Val Thr Gln Leu Asn Arg Cys Ala Ala His Pro
            20                  25                  30

Pro Tyr Ala Ser Trp Arg Asn Ser Glu Glu Ala Arg Thr Asp Arg Pro
        35                  40                  45

Ser Gln Gln Leu
    50

<210> SEQ ID NO 3
<211> LENGTH: 52
<212> TYPE: PRT
<213> ORGANISM: E.coli

<400> SEQUENCE: 3

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Gln Glu Ala Arg Thr Asp Arg Pro
        35                  40                  45

Ser Gln Gln Leu
    50

<210> SEQ ID NO 4
<211> LENGTH: 52
<212> TYPE: PRT
<213> ORGANISM: E.coli

<400> SEQUENCE: 4

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala Arg Thr Asp Arg Pro
        35                  40                  45

Ser Gln Gln Leu
    50

<210> SEQ ID NO 5
<211> LENGTH: 43
<212> TYPE: PRT
<213> ORGANISM: E.coli

<400> SEQUENCE: 5

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asp Ser Glu Glu Ala
        35                  40

<210> SEQ ID NO 6
<211> LENGTH: 993
<212> TYPE: PRT
<213> ORGANISM: E.coli

<400> SEQUENCE: 6

```
Met Gly Val Ile Thr Asp Ser Leu Ala Val Ala Arg Thr Asp Arg
 1               5                  10                  15

Pro Ser Gln Gln Leu Arg Ser Leu Asn Gly Glu Trp Arg Phe Ala Trp
            20                  25                  30

Phe Pro Ala Pro Glu Ala Val Pro Glu Ser Trp Leu Glu Cys Asp Leu
        35                  40                  45

Pro Glu Ala Asp Thr Val Val Val Pro Ser Asn Trp Gln Met His Gly
    50                  55                  60

Tyr Asp Ala Pro Ile Tyr Thr Asn Val Thr Tyr Pro Ile Thr Val Asn
65                  70                  75                  80

Pro Pro Phe Val Pro Thr Glu Asn Pro Thr Gly Cys Tyr Ser Leu Thr
                85                  90                  95

Phe Asn Val Asp Glu Ser Trp Leu Gln Glu Gly Gln Thr Arg Ile Ile
            100                 105                 110

Phe Asp Gly Val Asn Ser Ala Phe His Leu Trp Cys Asn Gly Arg Trp
        115                 120                 125

Val Gly Tyr Gly Gln Asp Ser Arg Leu Pro Ser Glu Phe Asp Leu Ser
    130                 135                 140

Ala Phe Leu Arg Ala Gly Glu Asn Arg Leu Ala Val Met Val Leu Arg
145                 150                 155                 160

Trp Ser Asp Gly Ser Tyr Leu Glu Asp Gln Asp Met Trp Arg Met Ser
                165                 170                 175

Gly Ile Phe Arg Asp Val Ser Leu Leu His Lys Pro Thr Thr Gln Ile
            180                 185                 190

Ser Asp Phe His Val Ala Thr Arg Phe Asn Asp Asp Phe Ser Arg Ala
        195                 200                 205

Val Leu Glu Ala Glu Val Gln Met Cys Gly Glu Leu Arg Asp Tyr Leu
    210                 215                 220

Arg Val Thr Val Ser Leu Trp Gln Gly Glu Thr Gln Val Ala Ser Gly
225                 230                 235                 240

Thr Ala Pro Phe Gly Gly Glu Ile Ile Asp Glu Arg Gly Gly Tyr Ala
                245                 250                 255

Asp Arg Val Thr Leu Arg Leu Asn Val Glu Asn Pro Lys Leu Trp Ser
            260                 265                 270

Ala Glu Ile Pro Asn Leu Tyr Arg Ala Val Val Glu Leu His Thr Ala
        275                 280                 285

Asp Gly Thr Leu Ile Glu Ala Glu Ala Cys Asp Val Gly Phe Arg Glu
    290                 295                 300

Val Arg Ile Glu Asn Gly Leu Leu Leu Leu Asn Gly Lys Pro Leu Leu
305                 310                 315                 320

Ile Arg Gly Val Asn Arg His Glu His His Pro Leu His Gly Gln Val
                325                 330                 335

Met Asp Glu Gln Thr Met Val Gln Asp Ile Leu Leu Met Lys Gln Asn
            340                 345                 350

Asn Phe Asn Ala Val Arg Cys Ser His Tyr Pro Asn His Pro Leu Trp
        355                 360                 365

Tyr Thr Leu Cys Asp Arg Tyr Gly Leu Tyr Val Val Asp Glu Ala Asn
    370                 375                 380

Ile Glu Thr His Gly Met Val Pro Met Asn Arg Leu Thr Asp Asp Pro
```

```
              385                 390                 395                 400
Arg Trp Leu Pro Ala Met Ser Glu Arg Val Thr Arg Met Val Gln Arg
                405                 410                 415

Asp Arg Asn His Pro Ser Val Ile Ile Trp Ser Leu Gly Asn Glu Ser
                420                 425                 430

Gly His Gly Ala Asn His Asp Ala Leu Tyr Arg Trp Ile Lys Ser Val
                435                 440                 445

Asp Pro Ser Arg Pro Val Gln Tyr Glu Gly Gly Ala Asp Thr Thr
450                 455                 460

Ala Thr Asp Ile Ile Cys Pro Met Tyr Ala Arg Val Asp Glu Asp Gln
465                 470                 475                 480

Pro Phe Pro Ala Val Pro Lys Trp Ser Ile Lys Lys Trp Leu Ser Leu
                485                 490                 495

Pro Gly Glu Thr Arg Pro Leu Ile Leu Cys Glu Tyr Ala His Ala Met
                500                 505                 510

Gly Asn Ser Leu Gly Gly Phe Ala Lys Tyr Trp Gln Ala Phe Arg Gln
                515                 520                 525

Tyr Pro Arg Leu Gln Gly Gly Phe Val Trp Asp Trp Val Asp Gln Ser
                530                 535                 540

Leu Ile Lys Tyr Asp Glu Asn Gly Asn Pro Trp Ser Ala Tyr Gly Gly
545                 550                 555                 560

Asp Phe Gly Asp Thr Pro Asn Asp Arg Gln Phe Cys Met Asn Gly Leu
                565                 570                 575

Val Phe Ala Asp Arg Thr Pro His Pro Ala Leu Thr Glu Ala Lys His
                580                 585                 590

Gln Gln Gln Phe Phe Gln Phe Arg Leu Ser Gly Gln Thr Ile Glu Val
                595                 600                 605

Thr Ser Glu Tyr Leu Phe Arg His Ser Asp Asn Glu Leu Leu His Trp
                610                 615                 620

Met Val Ala Leu Asp Gly Lys Pro Leu Ala Ser Gly Glu Val Pro Leu
625                 630                 635                 640

Asp Val Ala Pro Gln Gly Lys Gln Leu Ile Glu Leu Pro Glu Leu Pro
                645                 650                 655

Gln Pro Glu Ser Ala Gly Gln Leu Trp Leu Thr Val Arg Val Val Gln
                660                 665                 670

Pro Asn Ala Thr Ala Trp Ser Glu Ala Gly His Ile Ser Ala Trp Gln
                675                 680                 685

Gln Trp Arg Leu Ala Glu Asn Leu Ser Val Thr Leu Pro Ala Ala Ser
                690                 695                 700

His Ala Ile Pro His Leu Thr Thr Ser Glu Met Asp Phe Cys Ile Glu
705                 710                 715                 720

Leu Gly Asn Lys Arg Trp Gln Phe Asn Arg Gln Ser Gly Phe Leu Ser
                725                 730                 735

Gln Met Trp Ile Gly Asp Lys Lys Gln Leu Leu Thr Pro Leu Arg Asp
                740                 745                 750

Gln Phe Thr Arg Ala Pro Leu Asp Asn Asp Ile Gly Val Ser Glu Ala
                755                 760                 765

Thr Arg Ile Asp Pro Asn Ala Trp Val Glu Arg Trp Lys Ala Ala Gly
                770                 775                 780

His Tyr Gln Ala Glu Ala Ala Leu Leu Gln Cys Thr Ala Asp Thr Leu
785                 790                 795                 800

Ala Asp Ala Val Leu Ile Thr Thr Ala His Ala Trp Gln His Gln Gly
                805                 810                 815
```

```
                                    -continued

Lys Thr Leu Phe Ile Ser Arg Lys Thr Tyr Arg Ile Asp Gly Ser Gly
                820                 825                 830

Gln Met Ala Ile Thr Val Asp Val Glu Val Ala Ser Asp Thr Pro His
            835                 840                 845

Pro Ala Arg Ile Gly Leu Asn Cys Gln Leu Ala Gln Val Ala Glu Arg
        850                 855                 860

Val Asn Trp Leu Gly Leu Gly Pro Gln Glu Asn Tyr Pro Asp Arg Leu
865                 870                 875                 880

Thr Ala Ala Cys Phe Asp Arg Trp Asp Leu Pro Leu Ser Asp Met Tyr
                885                 890                 895

Thr Pro Tyr Val Phe Pro Ser Glu Asn Gly Leu Arg Cys Gly Thr Arg
                900                 905                 910

Glu Leu Asn Tyr Gly Pro His Gln Trp Arg Gly Asp Phe Gln Phe Asn
            915                 920                 925

Ile Ser Arg Tyr Ser Gln Gln Gln Leu Met Glu Thr Ser His Arg His
            930                 935                 940

Leu Leu His Ala Glu Glu Gly Thr Trp Leu Asn Ile Asp Gly Phe His
945                 950                 955                 960

Met Gly Ile Gly Gly Asp Asp Ser Trp Ser Pro Ser Val Ser Ala Glu
                965                 970                 975

Phe Gln Leu Ser Ala Gly Arg Tyr His Tyr Gln Leu Val Trp Cys Gln
            980                 985                 990

Lys

<210> SEQ ID NO 7
<211> LENGTH: 53
<212> TYPE: PRT
<213> ORGANISM: E. coli
<220> FEATURE:
<221> NAME/KEY: PEPTIDE
<222> LOCATION: (1)...(53)
<223> OTHER INFORMATION: alpha peptide (wildtype)

<400> SEQUENCE: 7

Met Gly Val Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg
    50
```

DETECTION OF MOLECULAR INTERACTIONS USING A REDUCED AFFINITY ENZYME COMPLEMENTATION REPORTER SYSTEM

CROSS-REFERENCE TO RELATED APPLICATIONS

Pursuant to 35 U.S.C. §119 (e), this application claims priority to the filing date of the U.S. Provisional Patent Application Ser. No. 60/782,054 filed Mar. 13, 2006; the disclosures of which application is herein incorporated by reference.

GOVERNMENT RIGHTS

This invention was made with government support under contracts HD018179; AG009521; AG024987; AG020961; and DAMB17-00-1-0442 awarded by the National Institutes of Health. The government has certain rights in this invention.

BACKGROUND

Molecular interactions, such as protein-protein interactions, are involved in almost every cellular process in living cells. Therefore, elucidating protein function is an important step toward understanding the mechanisms underlying biological pathways. Furthermore, the development of therapies for the treatment of human diseases and disorders depends upon the understanding of protein function in biological processes related to the disease or disorder. In addition, with the completion of the human genome sequencing project, the number of proteins identified with unknown function has increased dramatically. To elucidate a protein's function, it is useful to identify the interactions of a protein with other proteins.

As such, systems of identifying and characterizing protein-protein interactions, as well as modulators thereof, find wide application in a variety of different applications.

SUMMARY OF THE INVENTION

Methods and compositions for detecting molecular interactions are provided. Aspects of the invention include the use of a reduced affinity enzyme complementation reporter system. In certain embodiments, the reduced affinity enzyme complementation reporter system is a reduced affinity β-galactosidase complementation reporter system. Also provided are systems and kits for use in practicing embodiments of the methods.

Aspects of the invention include methods of determining whether a first and second protein interact. Embodiments of the methods include: (a) providing a cell comprising: (i) a first fusion protein of said first protein and a first β-galactosidase fragment, wherein the first β-galactosidase fragment is a variant minimal N-terminal β-galactosidase peptide; and (ii) a second fusion protein of said second protein and a second β-galactosidase fragment; wherein the first and second β-galactosidase fragments have an affinity for each other which provides a known level of β-galactosidase activity in the absence of an interaction between the first and second proteins that is lower than the activity observed in the presence of an interaction between the first and second proteins; and (b) evaluating the cell for β-galactosidase activity to determine whether said first and second proteins interact. In certain embodiments, the providing step comprises introducing nucleic acids encoding the first and second fusion proteins into the cell, where the nucleic acids may be introduced into the cell sequentially or simultaneously. In certain embodiments, the methods further include contacting the cell with a candidate interaction modulatory agent prior to the evaluating step. In certain embodiments, the evaluating step comprises comparing observed β-galactosidase activity to the known level of β-galactosidase activity. In certain embodiments, the first β-galactosidase fragment has a binding affinity for the second β-galactosidase fragment that is lower than a β-galactosidase fragment consisting of amino acids 3 to 92 of *E. coli* wild-type β-galactosidase. In certain embodiments, the first β-galactosidase fragment comprises at least one amino acid variation as compared to a β-galactosidase fragment consisting of amino acids 3 to 92 of *E. coli* wild-type β-galactosidase. In certain embodiments, the at least one amino acid variation is a substitution or a deletion. In certain embodiments, the variation occurs between residues 31 and 41. In certain embodiments, the cell is a mammalian cell. In certain embodiments, the interaction occurs at an intracellular location. In certain embodiments, the interaction occurs at a plasma-membrane location.

Aspects of the invention also include cells comprising: (a) a first fusion protein of a first protein and a first β-galactosidase fragment, wherein the first β-galactosidase fragment is a variant minimal N-terminal β-galactosidase peptide; and (b) a second fusion protein of a second protein and a second β-galactosidase fragment; wherein the first and second β-galactosidase fragments have a low affinity for each other that provides a known level of β-galactosidase activity in the absence of an interaction between said first and second proteins that is lower than the activity observed in the presence of an interaction between said first and second proteins. In certain embodiments, the first and second fusion proteins are intracellular proteins. In certain embodiments, at least one of the first and second fusion proteins is a membrane bound protein. In certain embodiments, both of the first and second fusion proteins are membrane bound proteins.

Also provided are kits that include (a) a cell comprising: (i) a first fusion protein of a first protein and a first β-galactosidase fragment, wherein the first β-galactosidase fragment is a variant minimal N-terminal β-galactosidase peptide; and (ii) a second fusion protein of said second protein and a second β-galactosidase fragment; wherein the first and second β-galactosidase fragments have a low affinity for each other which provides a known level of β-galactosidase activity in the absence of an interaction between the first and second proteins that is lower than the activity observed in the presence of an interaction between said first and second proteins; and (b) a β-galactosidase substrate. Also provided are kits comprising: (a) a first nucleic acid encoding a first β-galactosidase fragment; and (b) a second nucleic acid encoding a second β-galactosidase fragment; wherein the first β-galactosidase fragment is a variant minimal N-terminal β-galactosidase peptide and has a binding affinity for said second β-galactosidase fragment that is lower than a β-galactosidase fragment consisting of amino acids 3 to 92 of *E. coli* wild-type β-galactosidase. In certain embodiments, the first and second nucleic acids are present on vectors. In certain embodiments, the vectors comprise a restriction site positioned on the vector such that when a protein coding sequence is inserted into the vector using the restriction site, the vector encodes a fusion protein of the protein and a β-galactosidase fragment. In certain embodiments, the kit further comprises a cell. In certain embodiments, the kit further comprises a β-galactosidase substrate.

Schematic illustration of the low affinity α complementation system. Physical association of two chimeric proteins brings mutant β-gal fragments, M15 (ω) and H31Rα (α) into proximity, generating β-galactosidase activity. B) Low affinity α-complementation monitors strong protein interactions. Cells expressing FRBα* and FKBP12ω exhibited increased β-galactosidase activity after exposure to rapamycin (Rap). C) Low affinity α-complementation quantitatively monitors protein interactions such as the inducible interaction of the membrane bound β2-adrenergic receptor (B2AR) and cytosolic β-arrestin2 was monitored in cells expressing B2ARω and β-arrestin2α* chimeras. α* denotes chimeric proteins consisting of protein of interest-yellow fluorescence protein (YFP)-H31Rα fusions. D) Dose response of the interaction of B2ARω and β-arrestin2α* chimeras 45 minutes after exposure to the agonist isoproterenol assayed as β-gal activity. E) The B2ARω and β-arrestin2α* interaction was prevented in a dose dependent manner by the antagonist, propanolol. Increasing doses of propanolol were added to cells 10 min prior to addition of 10 μM isoproterenol, and β-gal activity was measured 45 min later. F-G) Low affinity α-complementation monitors heterodimer formation between the EGFR and ErbB2. The extracellular and transmembrane domains of the EGFR and ErbB2 were used to create two chimeras, EGFRω and ErbB2α*. G) Cells expressing both EGFRω and ErbB2α* were stimulated with 100 ng/ml EGF and the enzyme activity was measured, demonstrating increasing heterodimer formation over time. H) Low affinity α-complementation monitors the interaction of the EGFR and ErbB2 in a dynamic and reversible fashion. After stimulation of cells with either EGF or TGF-α, the excess ligand was removed (washout) and heterodimer dissociation was measured as a function of enzyme activity. The β-gal activity at steady state in cells in the presence of ligand was normalized to 100% and β-gal activity in cells in the absence of ligand was designated zero.

Figure 2:
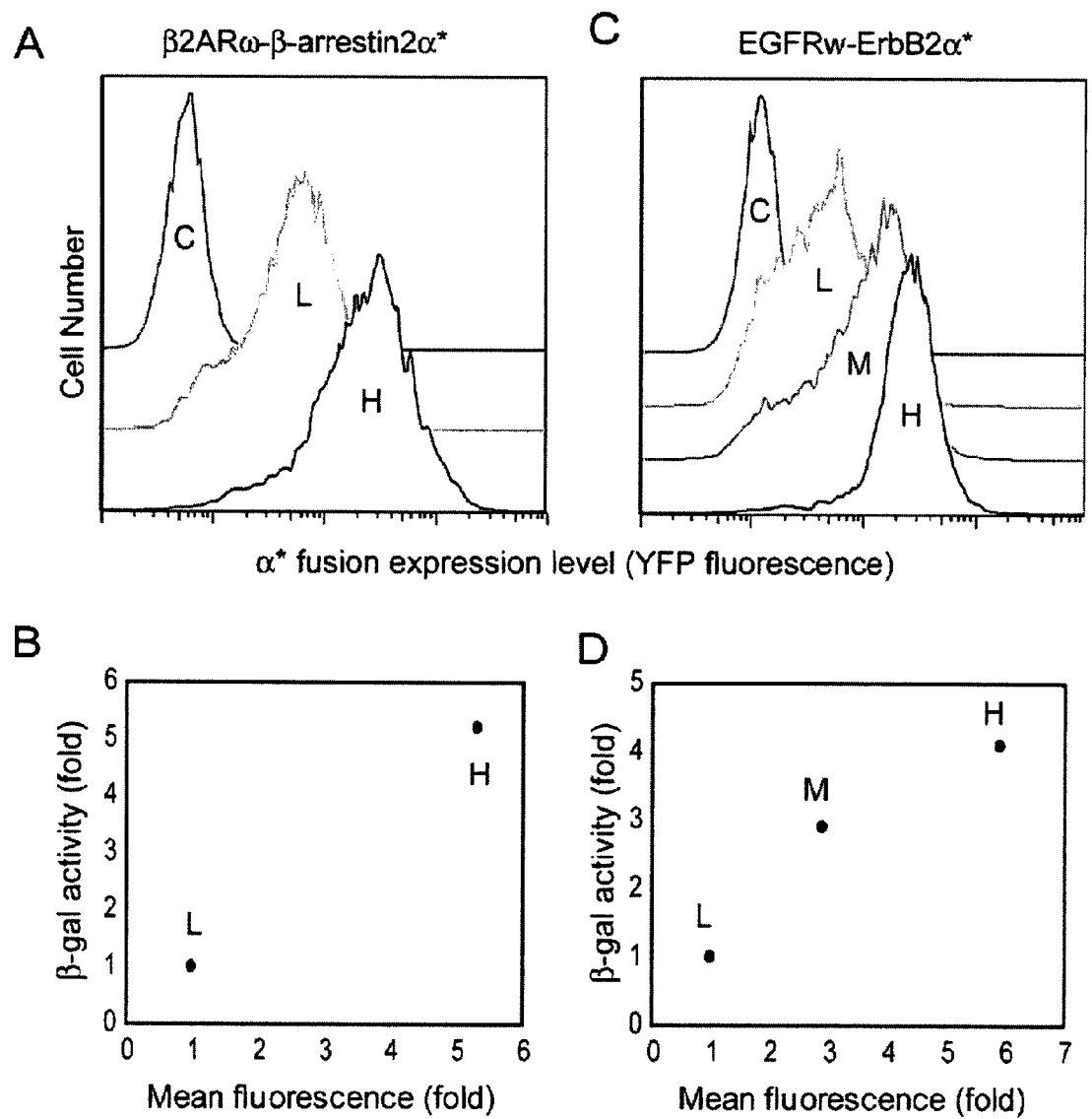

FIG. 2. Basal β-gal activity is dependent on the levels of expression of α and ω chimeras. A) The B2ARω-β-arrestin2α* and EGFRω-ErbB2α* cell lines were distinguished by flow cytometry based on levels of YFP fluorescence which served as an indicator of α* peptide levels. B) After sorting, equivalent numbers of cells from each cell line were plated into a 96-well dish and β-gal activity was measured in the absence of inducers. The enzyme activity is compared to fluorescence intensity with the lowest expressers scaled to 1 for fluorescence and β-gal activity. As the expression level of the α* peptide increases, the background β-gal activity increases.

Figure 3:
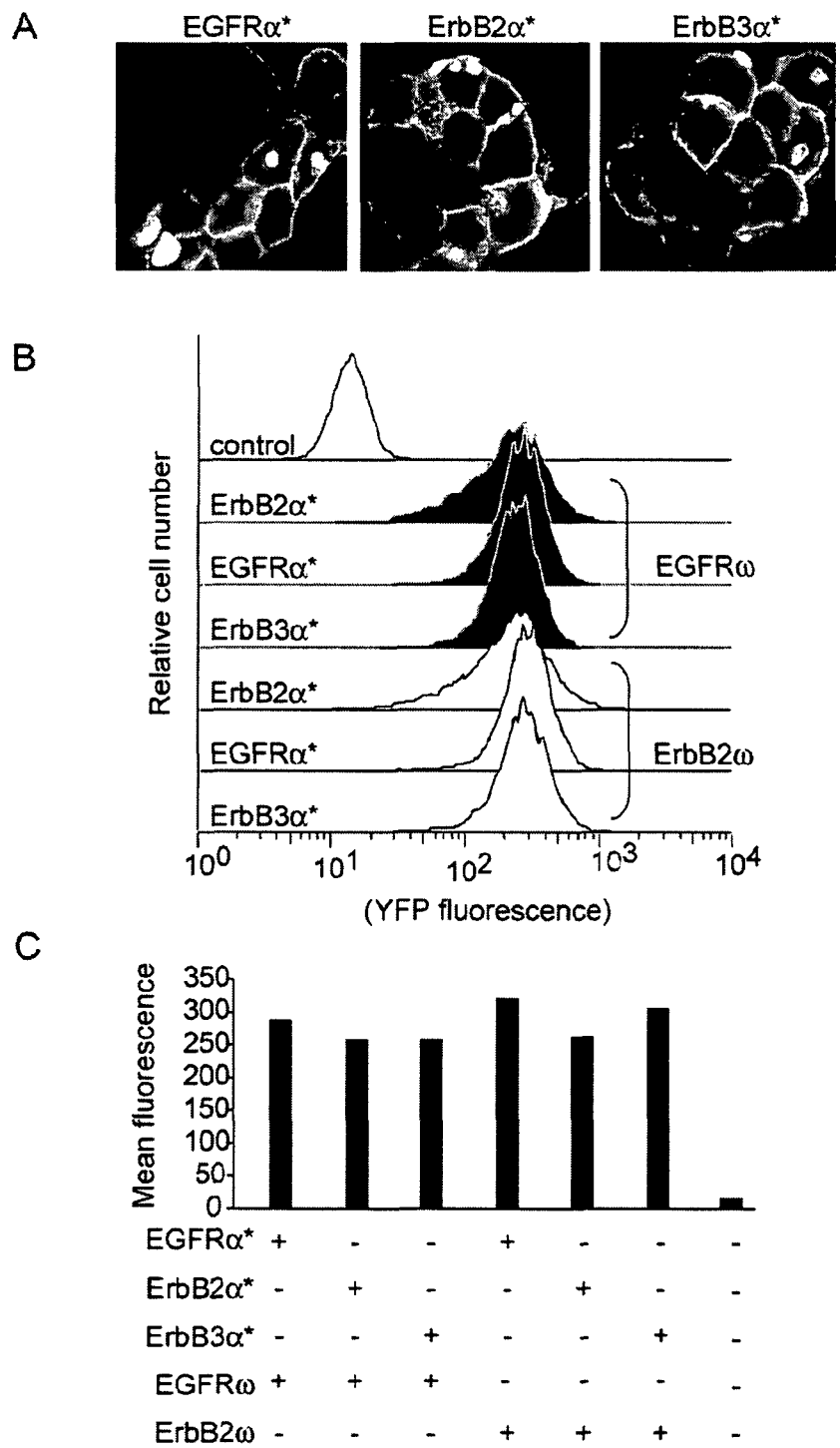

FIG. 3. Creation of cell lines with comparable α* and ω for profiling the basal and induced interactions of pairs of EGFR, ErbB2, and ErbB3 receptors. A) To ensure that all chimeras were similarly expressed and localized to the plasma membrane, the α* fusion constructs were transfected into HEK293 cells and imaged for YFP fluorescence by confocal microscopy. B) Two parental cell lines were created from C2C12 cells that express either the EGFRω or ErbB2ω. The parental lines were transduced with the α* chimeras and sorted for similar YFP expression levels. C) Quantitation of the mean fluorescence for each cell line shows less than a 15% variation among all six lines.

Figure 4:
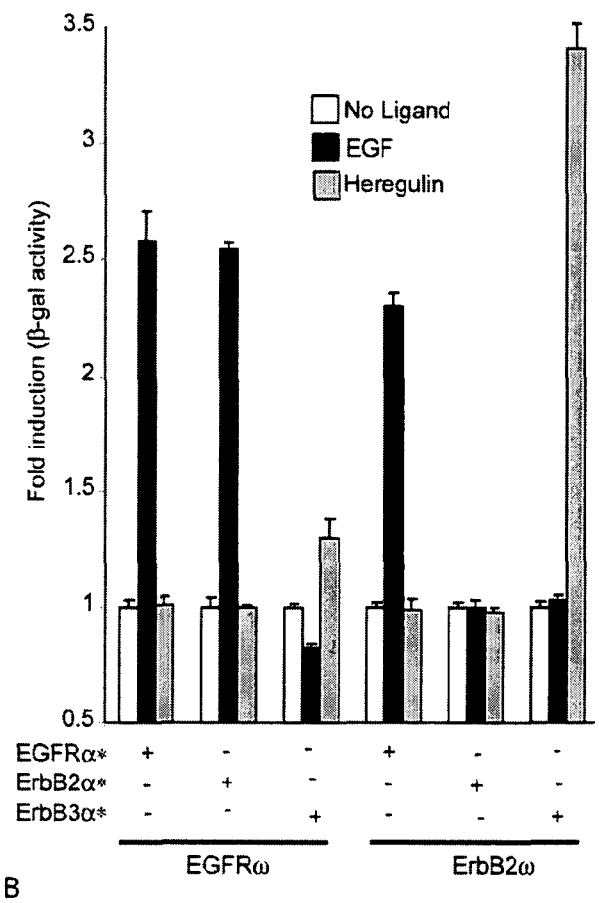
Figure 4:
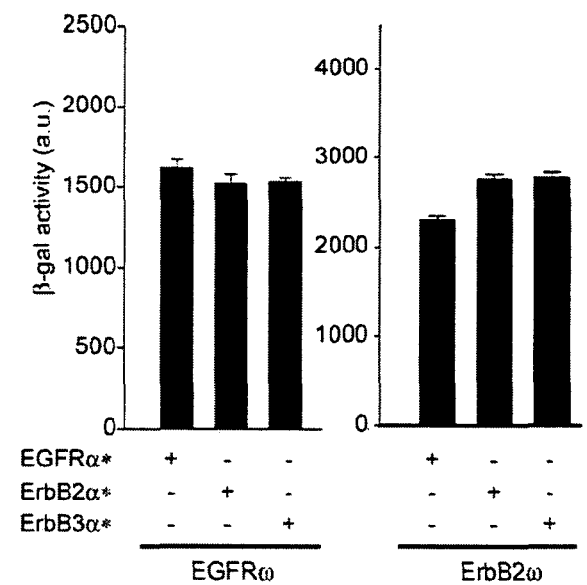

FIG. 4. Comparative analysis of the basal and induced interactions between the EGFR, ErbB2, and ErbB3. A) Aliquots of each of the six cell lines expressing different combinations of ErbB receptor chimeric proteins were plated into a 96-well dish at a density of 20,000 cells per well. The cells were stimulated with the indicated ligand for 45 min and β-gal activity was measured. Upon exposure to EGF, only EGFR homodimers and EGFR-ErbB2 heterodimers were formed, whereas Heregulin treatment resulted only in the formation of ErbB2-ErbB3 heterodimers. B) For each of the cell lines, the β-gal activity measured in the absence of ligand indicates basal dimerization levels. Note that ErbB2 does not exhibit an increased propensity to form homodimers relative to the EGFR or ErbB3.

Figure 1:
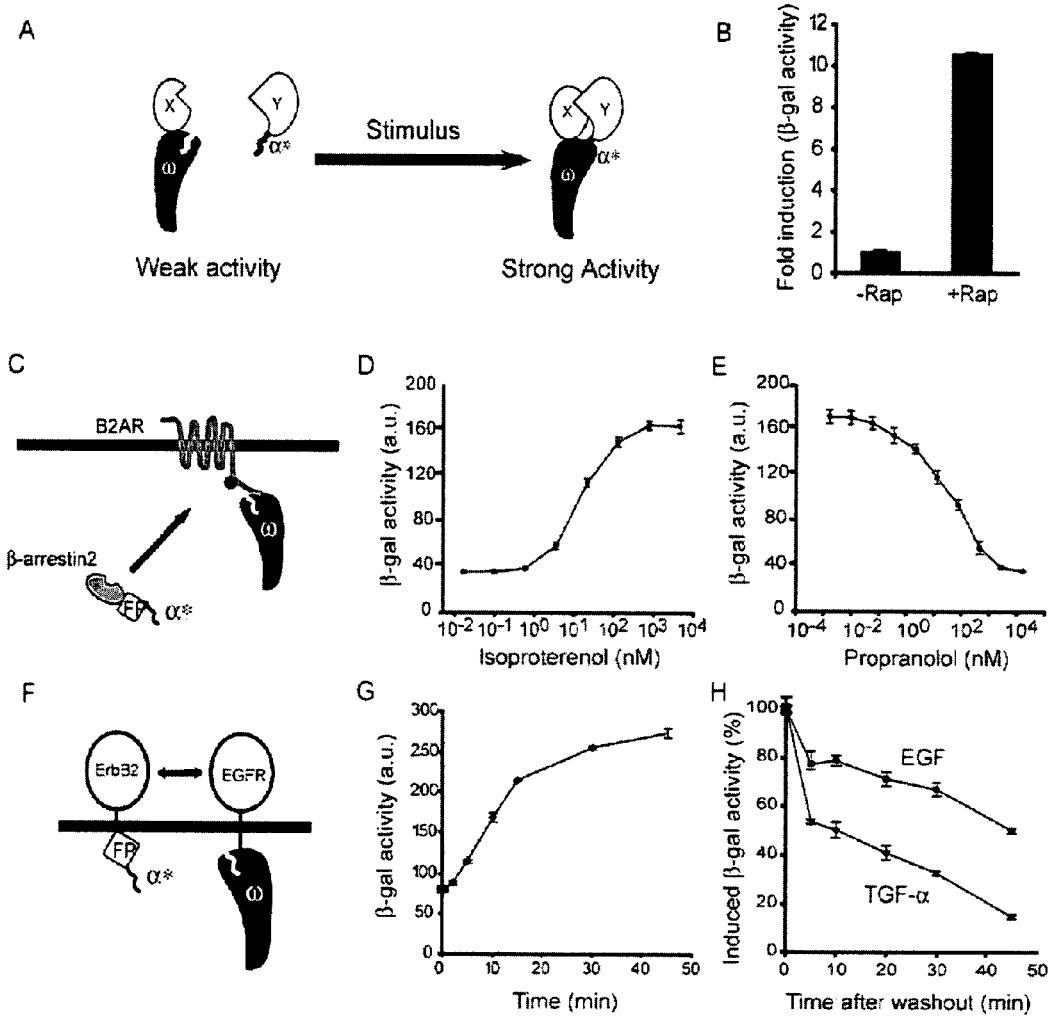
FIG. 1. Inducible protein interactions monitored by reduced affinity α-complementation of β-galactosidase. A)
Figure 5:
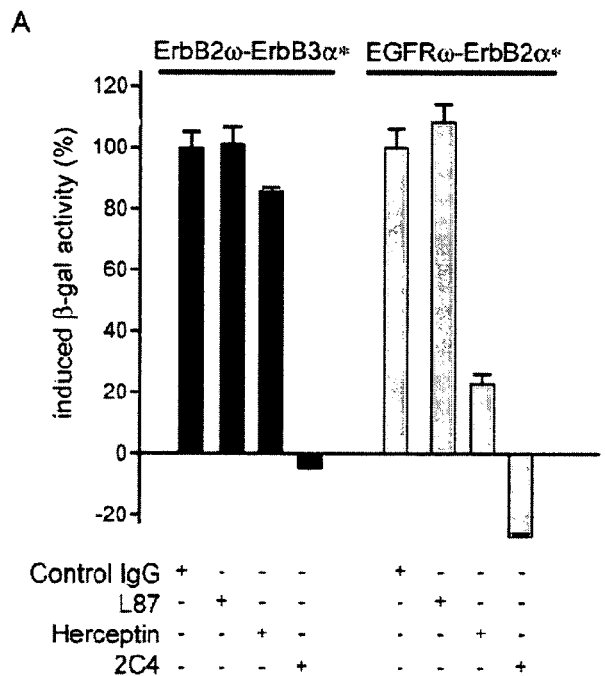
Figure 5:
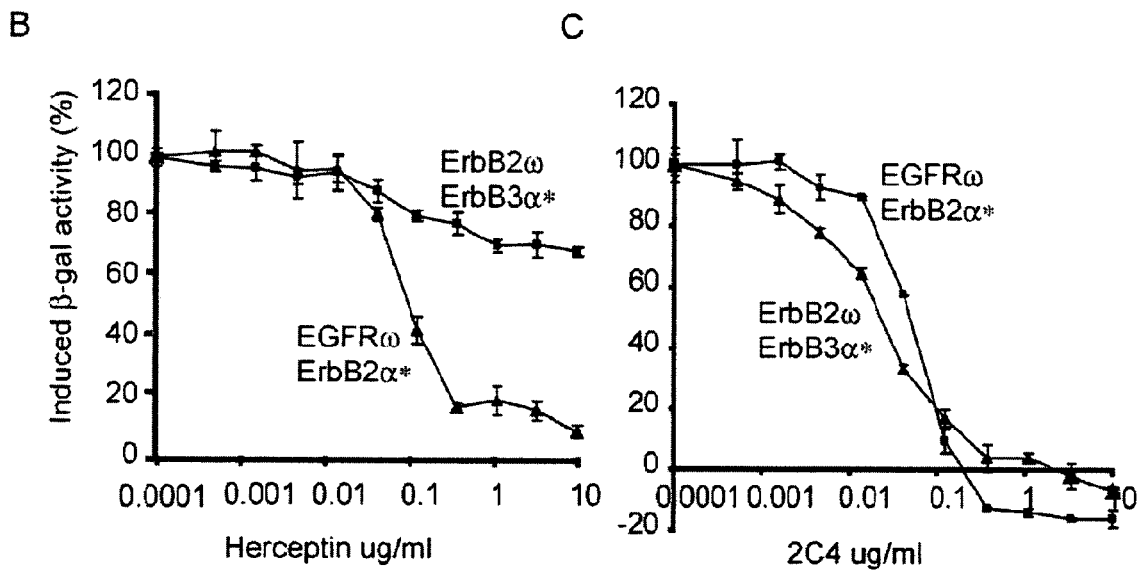

FIG. 5. Distinct effects of monoclonal antibodies on ErbB2 dimerization. A) The ErbB2ω-ErbB3α* and EGFRω-ErbB2α* cell lines were exposed to 1 ug/ml of the indicated antibodies for 30 min stimulated with the appropriate ligand and assayed for β-gal activity. The control IgG and the L87 antibody have no effect on ErbB2 interactions. The 2C4 antibody completely inhibits all ErbB2 interactions and Herceptin strongly inhibits the interaction of the EGFR and ErbB2, but only minimally affects the interaction of ErbB2 and ErbB3. B) Inhibition of ErbB2 interactions by Herceptin and 2C4 occurs at similar antibody concentrations. Cell lines were pretreated with different doses of the indicated monoclonal antibody prior to addition of 10 ng/ml of either EGF or heregulin (HRGβ1). In both A and B the data were normalized as described for FIG. 1H.

Figure 6:
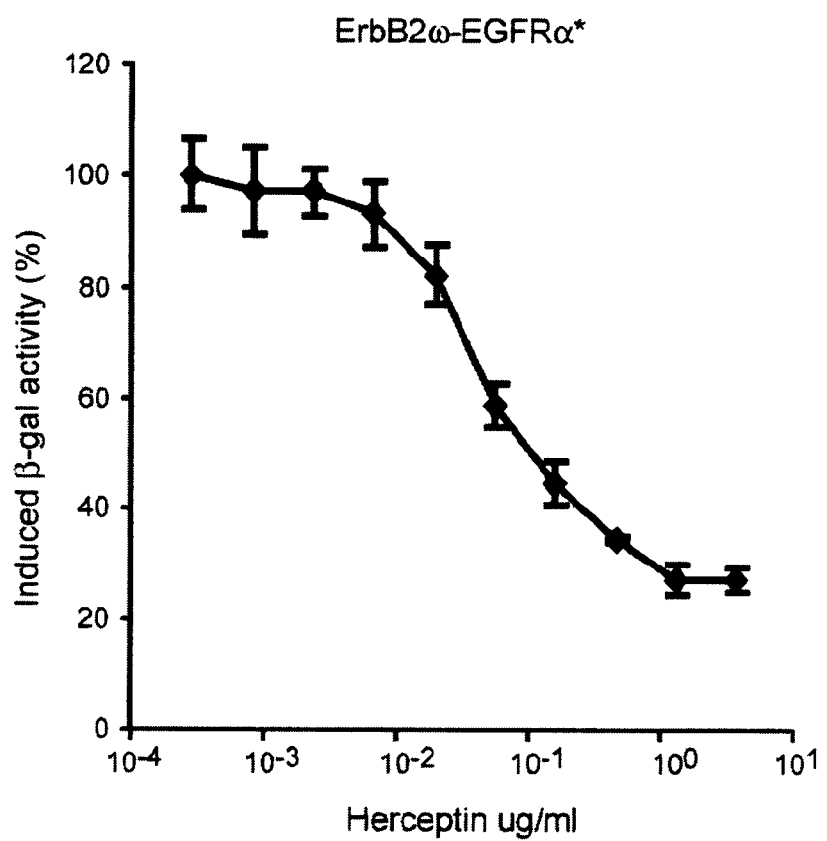

FIG. 6. The Herceptin mediated inhibition of EGFR-ErbB2 dimerization measured by β-gal activity is independent of the β-gal fragment (ω or α*) used to create the chimeric protein. FIG. 3 shows the inhibition of EGFRω and ErbB2α* heterodimerization in the presence of EGF. To ensure that this was not a result of the β-gal complementation system, the EGFRα* ErbB2ω cell line was also tested. Cells were treated with varying doses of Herceptin 30 minutes prior to EGF treatment.

Figure 7:
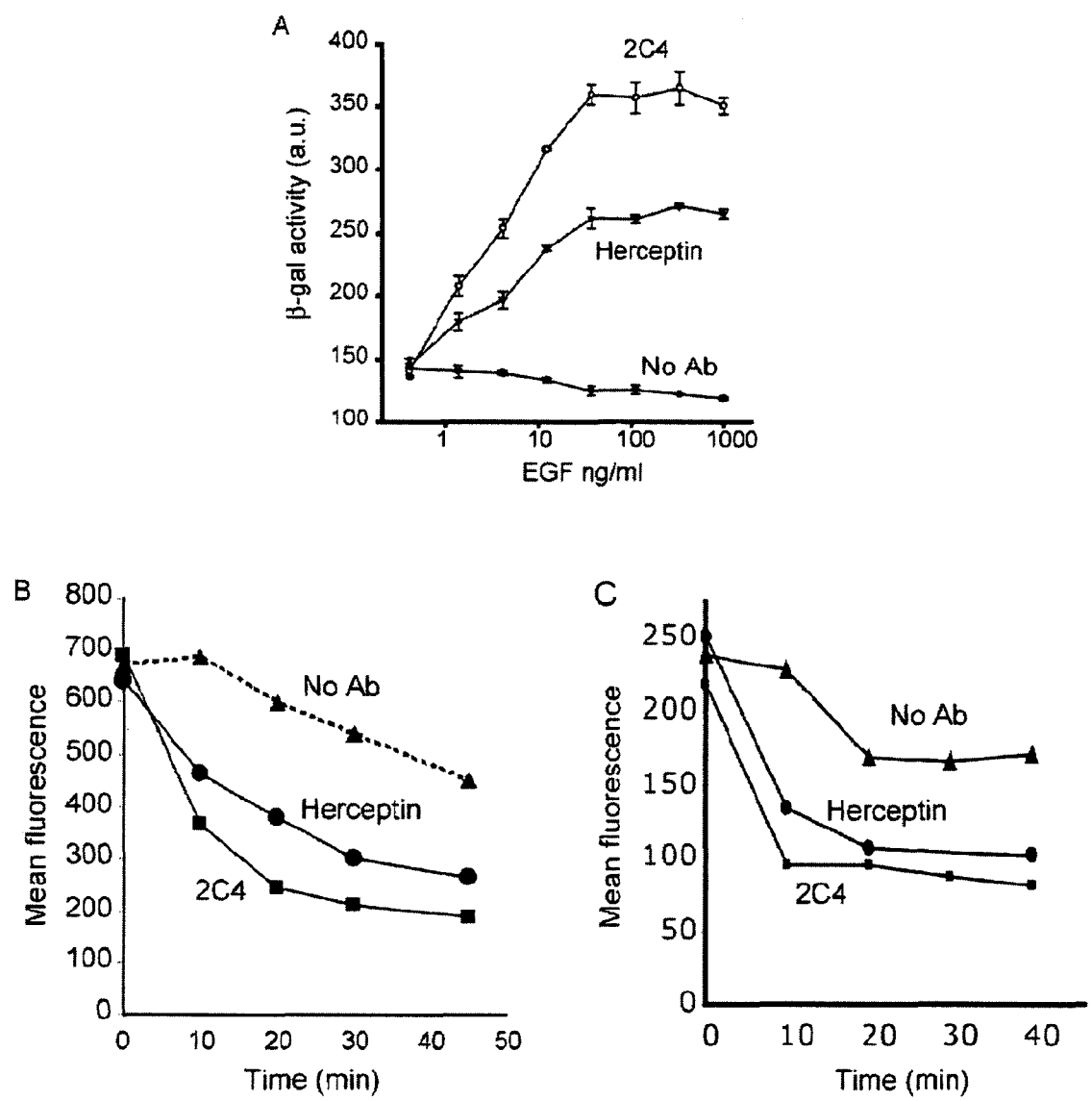

FIG. 7. Inhibition of EGFR-ErbB2 heterodimerization by Herceptin and 2C4 increases EGFR homodimer formation and internalization. A) C2C12 cells expressing the EGFRω, EGFRα*, as well as overexpressed wild-type ErbB2 (with no β-gal fragment) were treated with increasing concentrations of EGF. In the presence of excess ErbB2, heterodimer formation is favored and enzyme activity does not increase in response to EGF in the absence of antibody (No Ab). Herceptin and 2C4 inhibit the association of ErbB2 with the EGFR. Incubation with 1 ug/ml of each antibody prior to EGF treatment restores the ability of the EGFR to form homodimers. (B-C) Assay of EGFR internalization in response to antibody treatment. C2C12 cells overexpressing both the wild-type EGFR and ErbB2 (B) or the breast cancer cell line, SKBR3 that expresses both of these receptors (C), were stimulated with EGF at different time points, incubated with anti-EGFR antibody (Ab-11) and analyzed by flow cytometry. For the Herceptin and 2C4 curves, 5 ug/ml of each antibody was added 10 min prior to EGF for each time point. Each antibody caused a rapid decrease in EGFR presence on the cell surface as compared to controls (No Ab) in both cell lines.

DEFINITIONS

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed.

(1986)); "Immobilized Cells and Enzymes" (IRL Press, (1986)); B. Perbal, "A Practical Guide To Molecular Cloning" (1984).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, $\epsilon$-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552-59 is used.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides. As such, a "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

The term "oligonucleotide" as used herein denotes single-stranded nucleotide multimers of from about 10 to about 100 nucleotides and up to 200 nucleotides in length.

The term "polynucleotide" as used herein refers to single- or double-stranded polymers composed of nucleotide monomers of generally greater than about 100 nucleotides in length.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

A "vector" is a replicon, such as plasmid, phage or cosmid, to which another DNA segment may be attached so as to bring about the replication of the attached segment.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

"Optional" or "optionally" means that the subsequently described circumstance may or may not occur, so that the description includes instances where the circumstance occurs and instances where it does not.

"Contacting" means to bring or put together. As such, a first item is contacted with a second item when the two items are brought or put together, e.g., by touching them to each other.

DETAILED DESCRIPTION

Methods and compositions for detecting molecular interactions are provided. Aspects of the invention include the use of a reduced affinity enzyme complementation reporter system, such as a reduced affinity β-galactosidase complementation reporter system. Also provided are systems and kits for use in practicing embodiments of the methods.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, aspects of the methods are reviewed first in greater detail, followed by a review of different applications in which embodiments of the methods find use, as well as a review of various kits that find use in practicing certain embodiments of the invention.

Methods

As summarized above, embodiments of the invention provide methods of detecting molecular interactions between first and second molecules, e.g., such as protein-protein interactions. As such, embodiments of the invention provide methods of determining whether a first and a second molecule bind to each other, i.e., interact with each other. Molecular interactions that can be detected using the subject methods may include a variety of different types of molecules, where the molecules may be the same or different kinds of molecules. As such, in certain embodiments the molecular interaction of interest is an interaction between a first and second molecule that are the same types of molecule, e.g., both the first and second molecules are polypeptides (e.g., proteins). In yet other embodiments, the first and second molecules may be different types of molecules, e.g., where the first molecule is a polypeptide and the second molecule is a nucleic acid. In certain embodiments, the first and second molecules are polypeptides, e.g., proteins, such that the methods are methods of detecting protein-protein interactions.

As summarized above, embodiments of the invention are directed to methods of determining whether first and second binding members interact. The methods include providing a cell in which each of the binding members of interest are labeled with a different member of a reduced-affinity enzyme complementation reporter system. The cell is then evaluated for activity of the reporter enzyme, and the result of the evaluation is employed to determine whether the first and second binding members interact.

Aspects of the methods include the use of a reduced-affinity enzyme complementation reporter system. By "reduced-affinity" enzyme complementation reporter system is meant a system that is made up of two, or more fragments of an enzyme (i.e., reporter subunits) that by themselves lack any of the detectable activity (which may be directly or indirectly detectable) that is observed in their parent enzyme but when brought sufficiently close together, e.g., through random interaction or a binding member mediated interaction, give rise to a detectable amount of the activity of the parent enzyme. An aspect of the reduced affinity enzyme complementation reporter systems of the invention is that at least one of the reporter subunits employed in the system is a variant of a corresponding domain in its wild-type parent enzyme such that its interaction with the other subunits of the system is reversible under assay conditions, absent an interaction mediated by binding moieties of interest. As such, the reduced-affinity enzyme complementation reporter systems of the present invention provide for a first detectable signal in the absence of an interaction of interest that is less than a second detectable signal that is observed in the presence of an interaction of interest. For example, where the system is a β-galactosidase system (as reviewed in greater detail below), the system provides for a first detectable signal in the absence of an interaction of interest that is less than a second detectable signal that is observed in the presence of an interaction of interest. In addition, aspects of the invention include embodiments where the magnitude of the first signal under a given set of assay conditions of interest is known, and may determined at the time the second signal is detected or at some previous time, where the value of the previous detection is used as a reference. Embodiments of the reduced-affinity enzyme complementation reporter systems are characterized by providing high signal-to-noise ratios.

Reporter subunits which have sufficiently low binding affinity such that they exhibit reversible binding to each other absent a binding moiety mediated interaction, and yet are still capable of associating and generating a detectable signal upon the binding of molecular species attached to them, can be produced using a number of different approaches. In certain embodiments, a rational approach is employed in which a first reporter system that is made up of high affinity subunits is studied to identify those regions of the subunits that are responsible for the high affinity associate of the subunits. The identified region(s) is then varied in some way, e.g., by introducing point mutations, insertions or deletions into the region, to obtain a suitable low affinity subunit and thereby obtain a reduced affinity reporter system in which the subunits reversibly interact in the absence of any binding member mediated association. See e.g., the experimental section below, as well as U.S. patent application Ser. No. 11/132,764 filed on May 18, 2005 for a review of such a rational approach as employed with an initial high affinity β-galactosidase complementation reporter system. Reporter subunits which can be used include any reduced binding affinity subunits which are capable of associating to produce a detectable signal. In one embodiment, the reporter subunits are proteins which are capable of associating and are capable when associated of catalyzing a reaction which produces a directly or indirectly detectable product.

Reduced affinity enzyme complementation reporter systems that are used in certain embodiments of the invention can employ reporter subunits derived from a number of different enzymes. Enzymes of interest from which reporter subunits may be derived include, but are not limited to: β-galactosidase, β-glucuronidase (GUS), β-lactamase, alkaline phosphatase, peroxidase, chloramphenicol acetyltransferase (CAT), cre-recombinase and luciferase.

In certain embodiments, the enzyme upon which the reduced-affinity enzyme complementation reporter system is based is wild-type $E.\ coli$ β-galactosidase, which is encoded by the $E.\ coli$ lacZ gene. β-galactosidase activity may be measured by a range of methods including live-cell flow cytometry and histochemical staining with the chromogenic substrate 5-bromo-4-chloro-3-indolyl β-D-galactopyranoside (X-Gal). See e.g., Nolan et al., Proc. Natl. Acad. Sci., USA, 85:2603-2607 (1988); and Lojda, Z., Enzyme Histochemistry: A Laboratory Manual, Springer, Berlin, (1979).

For illustrative purposes only, the invention is now further described primarily in terms of embodiments in which the reduced affinity enzyme complementation reporter system is a β-galactosidase enzyme complementation reporter system, i.e., where the reporter subunits are β-galactosidase fragments, where the fragments may have amino acid sequences found in their corresponding wild-type β-galactosidase molecules or have sequences that are variants of sequences found in their corresponding wild-type β-galactosidase molecules.

In certain embodiments, the employed reduced affinity β-galactosidase complementation reporter system is one that is made up of two or more β-galactosidase fragments or variants thereof. For example, in certain embodiments, the reporter system includes a first and second fragment of β-galactosidase (e.g., an α and ω fragment). In yet other embodiments, the reporter system may include more than two β-galactosidase fragments, such as a first, second and third β-galactosidase fragments (e.g., an α, β and ω fragment).

In certain embodiments, the reduced-affinity β-galactosidase complementation signal producing system employed in embodiments of the subject methods is one that is made up of first and second fragments of β-galactosidase (i.e., first and second β-galactosidase fragments), where the first and second fragments have an affinity for each other that provides for different levels of β-galactosidase activity depending on whether the polypeptide-polypeptide interaction of interest has occurred. As such, the first and second β-galactosidase fragments have an affinity for each other that provides a known first level of β-galactosidase activity in the absence of interaction of interest and a second, different level of β-galactosidase activity in the presence of the interaction of interest. In this manner, by determining the activity level of the signal producing system, a determination can be made as to whether the interaction of interest has occurred.

The first and second β-galactosidase fragments are ones that have a low affinity for each other, where the low affinity is sufficient to provide for differing interaction dependent activity levels reviewed above. As the fragments of the signal producing system have a low affinity for each other, the activity level (as determined using the assay reported in the Experimental Section below) that is observed from the system made up of the fragments in the absence of a polypeptide interaction of interest is less than the activity level that is observed in the absence of an interaction of interest with the β-galactosidase complementation system reported in Langley et al., Proc. Nat'l Acad. Sci. USA (1975) 72: 1254-1257.

Aspects of these embodiments include the use of a first β-galactosidase fragment (also known as an enzyme donor or a fragment) that is a variant minimal N-terminal β-galactosidase peptide. By minimal N-terminal β-galactosidase peptide is meant that the peptide has an amino acid sequence that is found in the N-terminal region of a wild-type β-galactosidase protein, e.g., a sequence that starts within about 10 residues of the N-terminus, such as within about 5 residues of the N-terminus of a wild-type β-galactosidase protein. As the first β-galactosidase fragments of this embodiment are minimal, they are, in certain embodiments, about 60 amino acids or less in length, such as about 55 amino acids in length or less, including about 50 amino acids or less in length, e.g., 49 amino acids or less in length, 48 amino acids or less in length, etc.

As the minimal N-terminal β-galactosidase peptides are variant, they include at least one sequence variation as compared to the corresponding sequence in the N-terminal domain of the corresponding wild-type β-galactosidase protein. The sequence variation may be an insertion, deletion or substitution, e.g., in the form of a point mutation. The variant may have a single variation (e.g., insertion, deletion, point mutations) or two or more different variations, such as two or more point mutations, etc. In certain embodiments, the first β-galactosidase fragment has a binding affinity for the second β-galactosidase fragment (described in greater detail below) which is less than the binding affinity of a fragment having the complete sequence from amino acid residue 3 to 92 (e.g., as described in Langley et al., J. Biol. Chem. (1975) 250:2587-2592) of wild-type E. coli β-galactosidase for the second β-galactosidase fragment, e.g., where the binding affinity is less than the wild-type fragment for the second β-galactosidase fragment.

In certain embodiments, any variation in sequence occurs in a region of the β-galactosidase fragment that, upon complementation of the fragment with the second fragment of the system, is in a "buried" location within the second β-galactosidase fragment. In certain embodiments, this domain includes the sequence found from amino acid residue 29 to 41 of the wild-type sequence, and therefore the fragment includes a variation in this region, e.g., from amino acid residue 29 to 41, such as from amino acid residue 31 to 41. For example, where the variations are point mutations, the variant may include one or more point mutations at any of amino acid residues 29 to 41, such that one or more of these 13 amino acid residues may be substituted, including 2 or more, three or more, four or more etc., of these amino acid residues may be substituted. Specific amino acid point mutations of interest include, but are not limited to: H31 (e.g., H31R); F34 (e.g., F34Y); E41 (e.g., E41Q); and N39 (e.g., N39Q, N39D).

Exemplary α peptide sequences include:

```
SEQ ID NO: 1 (H31R)
MGVITDSLAVVLQRRDWENPGVTQLNRLAARPPFASWRNSEEARTDRPSQ
QL

SEQ ID NO: 2 (F34Y)
MGVITDSLAVVLQRRDWENPGVTQLNRCAAHPPYASWRNSEEARTDRPSQ
QL

SEQ ID NO: 3 (E41Q)
MGVITDSLAVVLQRRDWENPGVTQLNRLAAHPPFASWRNSQEARTDRPSQ
QL

SEQ ID NO: 4 (N39D)
MGVITDSLAVVLQRRDWENPGVTQLNRLAAHPPFASWRDSEEARTDRPSQ
QL

SEQ ID NO: 5 (Truncated)
MGVITDSLAVVLQRRDWENPGVTQLNRLAAHPPFASWRDSEEA
```

In embodiments where the first fragment is a variant minimal N-terminal β-galactosidase fragment, as reviewed above, the first fragment may be used in conjunction with one or more additional fragments, as reviewed above. In certain embodiments as reviewed above, the reporter system is made up of a first and a second β-galactosidase fragment. The second β-galactosidase fragment may be any fragment that is capable of interacting with the first β-galactosidase fragment to provide for detectable β-galactosidase activity. The second β-galactosidase fragment may include a major portion of the β-galactosidase enzyme, corresponding to greater than about 60%, greater than about 80%, or greater than about 90% of the full-length β-galactosidase enzyme, based on molecular weight of the full-length β-galactosidase enzyme. In certain embodiments, the second β-galactosidase fragment is a deletion mutant that is missing aa 11-41 of the wild type E. coli β-galactosidase protein (e.g., as described in Langley et al., Proc. Nat'l Acad. Sci. USA (1975) 72: 1254-1257), which fragment is known as the M15 acceptor or ω fragment. Other specific acceptors (i.e., co-fragments) of interest include, but are not limited to: the M112 dimer, a deletion of amino acids 23-31 within β-galactosidase (Lin, Villarejo and Zabin, 1970, Biochem. Biophys. Res. Common. 40:249; Celeda and Zabin, 1979, Biochem. 18:404; Welphy, Fowler and Zabin, 1981, J. Biol. Chem. 256:6804; Langley et al., 1975, Proc. Natl. Acad. Sci. USA 72:1254). One exemplary ω peptide sequence is set forth below (SEQ ID NO:6):

```
MGVITDSLAVVARTDRPSQQLRSLNGEWRFAWFPAPEAVPESWLECDLPE
ADTVVVPSNWQMHGYDAPIYTNVTYPITVNPPFVPTENPTGCYSLTFNVD
ESWLQEGQTRIIFDGVNSAFHLWCNGRWVGYGQDSRLPSEFDLSAFLRAG
ENRLAVMVLRWSDGSYLEDQDMWRMSGIFRDVSLLHKPTTQISDFHVATR
FNDDFSRAVLEAEVQMCGELRDYLRVTVSLWQGETQVASGTAPFGGEIID
ERGGYADRVTLRLNVENPKLWSAEIPNLYRAVVELHTADGTLIEAEACDV
GFREVRIENGLLLLNGKPLLIRGVNRHEHHPLHGQVMDEQTMVQDILLMK
QNNFNAVRCSHYPNHPLWYTLCDRYGLYVVDEANIETHGMVPMNRLTDDP
RWLPAMSERVTRMVQRDRNHPSVIIWSLGNESGHGANHDALYRWIKSVDP
SRPVQYEGGGADTTATDIICPMYARVDEDQPFPAVPKWSIKKWLSLPGET
RPLILCEYAHAMGNSLGGFAKYWQAFRQYPRLQGGFVWDWVDQSLIKYDE
NGNPWSAYGGDFGDTPNDRQFCMNGLVFADRTPHPALTEAKHQQQFFQFR
LSGQTIEVTSEYLFRHSDNELLHWMVALDGKPLASGEVPLDVAPQGKQLI
ELPELPQPESAGQLWLTVRVVQPNATAWSEAGHISAWQQWRLAENLSVTL
PAASHAIPHLTTSEMDFCIELGNKRWQFNRQSGFLSQMWIGDKKQLLTPL
RDQFTRAPLDNDIGVSEATRIDPNAWVERWKAAGHYQAEAALLQCTADTL
ADAVLITTAHAWQHQGKTLFISRKTYRIDGSGQMAITVDVEVASDTPHPA
RIGLNCQLAQVAERVNWLGLGPQENYPDRLTAACFDRWDLPLSDMYTPYV
FPSENGLRCGTRELNYGPHQWRGDFQFNISRYSQQQLMETSHRHLLHAEE
GTWLNIDGFHMGIGGDDSWSPSVSAEFQLSAGRYHYQLVWCQK.
```

Aspects of the invention include the use of the reduced-affinity reporter systems described above to detect molecular interactions, i.e., interactions between two or more molecules (where the molecules are referred to herein as binding moieties or putative binding moieties). In using the reporter systems to detect molecular interactions between two or more binding moieties, in certain embodiments a cell is provided that includes each of the different binding moieties of interest stably associated with a different member of the reporter system. In other words, a cell is provided in which each binding moiety of interest is stably associated with a different subunit of the reporter system. For example, where the system is employed to detect the interaction between a first and second protein, a cell is provided that includes the first protein is stably associated with a first reporter subunit, e.g., the variant minimal N-terminal β-galactosidase fragment described above, while the second protein is stably associated with a second reporter subunit, e.g., the M15 ω fragment described above.

By stably associated is meant that the reporter subunit and the molecular entity are bound to each other, either covalently or otherwise, e.g., via a sufficiently high affinity interaction, such that they do not disassociate from each other under the assay conditions in which they are employed, as further illustrated below.

A multitude of different binding moieties can be assayed for their binding affinity with each other using the subject invention, where binding moieties include any molecules capable of a binding interaction. The binding interaction between the two or more binding moieties may be either direct or in the form of a complex with one or more additional binding species, such as charged ions or molecules, ligands or macromolecules.

The binding moieties which are stably associated with (i.e., attached to) the reporter subunit can be any of a range of different molecules including carbohydrates, lipids, proteins, and nucleic acids, as well as portions, polymers and analogues thereof, provided they are capable of being linked to the reporter subunit. In certain embodiments, the binding moieties of interest are intracellular moieties, such that the binding interaction that is detected is an intracellular interaction, e.g., that occurs in a non-spatially constrained manner. In yet other embodiments, the binding moieties of interest are plasma membrane moieties, such that the binding interaction that is detected is one that occurs at a plasma-membrane location in a spatially-constrained (e.g., two-dimensional) manner.

Exemplary proteins include members of a signal transduction cascade, proteins regulating apoptosis, proteins that regulate progression of the cell-cycle or development of tumors, transcriptional regulatory proteins, translational regulatory proteins, proteins that affect cell interactions, cell adhesion molecules (CAMs), ligand-receptor pairs, proteins that participate in the folding of other proteins, and proteins involved in targeting to particular intracellular compartments, such as the Golgi apparatus, endoplasmic reticulum, ribosomes, chloroplasts and mitochondria. Other exemplary proteins include protein hormones and cytokines. Cytokines include those involved in signal transduction, such as interferons, chemokines, and hematopoietic growth factors. Other exemplary proteins include interleukins, lymphotoxin, transforming growth factors-α and β, and macrophage and granulocyte colony stimulating factors. Other proteins include intracellular enzymes such as protein kinases, phosphatases and synthases. Exemplary proteins involved in apoptosis include tumor necrosis factor (TNF), Fas ligand, interleukin-1β converting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

Binding of molecules will depend upon factors in solution such as pH, ionic strength, concentration of components of the assay, and temperature. In the binding assays using reporter systems described herein, the binding affinity of the binding moieties should be high enough to permit complementation between the reporter subunits. Non-limiting examples of dissociation constants of the binding moieties in an assay solution, such as a buffered system or cell interior, are on the order of less than about $10^{-8}$ M, for example, less than about $10^{-9}$ M, or optionally, between about $10^{-9}$ to $10^{-12}$ M, depending upon the properties of the particular assay system.

As mentioned above, the reporter subunit and binding member are stably associated. In certain embodiments, the reporter subunit and one or more binding moieties are linked together, either directly or via a linker, where the linkage may or may not be a covalent linkage. For example, when the reporter subunit and the binding moiety are proteins, they may be linked by methods known in the art for linking peptides, e.g., expressed from a nucleic acid sequence as a fusion protein, as reviewed in greater detail below.

A given cell employed in a method of the invention can be provided using any convenient protocol. For example, conjugates of the different binding members and reporter subunits can be introduced into a cell using a number of different protocols, e.g., microinjection, electroporation or a variety of bulk-loading techniques, or by providing in the cell nucleic acids that encode the different elements, e.g., in the form of fusion proteins.

In certain embodiments, the reporter subunit and the binding moiety may make up a fusion protein that includes a reporter subunit, e.g., a variant minimal N-terminal β galactosidase peptide or an ω peptide as reviewed above. The fusion protein can thus be expressed from an encoding nucleic acid intracellularly. This system is advantageous in certain embodiments since it permits the detection and quantitation of protein-protein interactions in cells, such as mammalian cells, based on enzymatic complementation of the reporter subunits. For example, in the embodiment wherein chimeric fused proteins are produced intracellularly that include one of two complementing reporter subunits and a "test" protein of interest, the detected activity due to interactions between two chimeric proteins of interest will be proportional to the strength of the interaction of the reporter subunit (e.g., non-enzyme) protein components. Thus, the interaction is driven by the test proteins of interest, not the complementing reporter subunits. The enzymatic activity serves as an indicator of that interaction. Another advantage of this system is that only low levels of expression of the test proteins are required to detect binding.

In certain embodiments, the fusion gene constructs are constructed and transformed into cells to produce a first, e.g., low, level expression, where this low level expression is the result of the non-binding moiety mediated reversible association of the reporter subunits. The system then permits the monitoring of interactions in a given cell in the presence of endogenous competing protein partners, where the fusion protein will function as a "tracer" for the binding/association reaction. Such a system is not prone to artifacts arising from over-expression of introduced proteins. Reduction in expression of fusion gene constructs can be accomplished by choice of appropriate promoters, ribosome binding sites and other regulatory elements. For example, fusion gene constructs can be introduced into vectors in which they lie upstream of an antibiotic resistance gene whose translation is regulated by the Encephalomyocarditis virus internal ribosome entry sequence (IRES), and which contain a mutation in the splice donor/acceptor sequences upstream of the ATG sequence responsible for translational initiation of the fusion gene. This type of construct results in a lower translation efficiency of the first coding sequence in a bicistronic message, but does not affect translation of the second (antibiotic resistance) sequence, which is solely dependent on the IRES. As a result of these reduced levels of expression, the frequency of spontaneous interaction of reporter subunits, which is concentration-dependent, will be significantly reduced.

Aspects of the invention include fusion proteins between a putative binding moiety and a reporter subunit of the invention. The putative binding moiety may include any protein or other molecule whose ability to bind to a second molecule is to be tested. The reporter subunit may be any molecule wherein the monomer subunit is inactive, but association of two or more identical or different monomers restores activity, e.g., where the activity provides a detectable signal.

Fusion proteins of embodiments of the invention include a single continuous linear polymer of amino acids which includes the full or partial sequence of two or more distinct proteins. Two or more amino acids sequences may be joined chemically, for instance, through the intermediacy of a cross-linking agent. In certain embodiments, a fusion protein is generated by expression of a fusion gene construct in a cell. A fusion gene construct includes a single continuous linear polymer of nucleotides which encodes the full or partial sequences of two or more distinct proteins in the same uninterrupted reading frame. Fusion gene constructs also may contain replication origins active in eucaryotic and/or procaryotic cells and one or more selectable markers encoding, for example, drug resistance. They may also contain viral packaging signals as well as transcriptional and/or translational regulatory sequences and RNA processing signals.

In certain embodiments, the fusion gene constructs of the invention are introduced into cells to assay for binding between the putative binding moieties encoded by the fusion gene constructs. The fusion gene constructs may also contain promoters and other transcriptional and/or translational regulatory sequences that are normally associated with the gene encoding the putative binding moiety. The fusion gene constructs may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors of interest include, but are not limited to: retroviruses, poxviruses, herpesviruses, adenoviruses, and adeno-associated viruses. In certain embodiments, retroviral vectors are employed, which are capable of stable integration into the genome of the host cell. For example, retroviral constructs encoding integration and packaging signals, drug resistance markers and one or more fusion genes of interest are useful in the practice of embodiments of the invention.

Different fusion gene constructs encoding unique fusion proteins may be present on separate nucleic acid molecules or on the same nucleic acid molecule. In certain embodiments, the same vector is employed so that uptake of only a single species of nucleic acid by a cell is sufficient to introduce sequences encoding both putative binding partners into the cell. In terms of order of introduction, in those embodiments where the coding sequences are on different vectors, the vectors may be introduced into the cell simultaneously or sequentially.

The fusion gene constructs or fusion proteins of the invention may be introduced into cultured cells, animal cells in vivo, animal cells ex vivo, or any other type of cell in which it is desired to study protein-protein interactions. As such, cells that find use in practicing the present invention include prokaryotic and eukaryotic cells, where exemplary eukaryotic cells include mammalian cells (e.g., murine, feline, canine, human, etc.), yeast cells, parasite cells, etc. In certain embodiments, the cells are mammalian cells that have a particular phenotype, including primary normal, neoplastic or cancerous cells, and established cell lines (e.g., immortalized tumor cell lines).

Following provision of the cell comprising the different binding members of interest each tagged (i.e., labeled) with a different subunit of the reporter system, the cell is then evaluated for activity of the reporter system, where the result of this evaluation step provides information about whether a binding interaction of interest has taken place. In certain embodiments, evaluation includes detecting the activity and then comparing the observed activity to a reference or control value, e.g., a previously determined background activity value, such as a level of β-galactosidase activity that is observed solely as a result of the reversible interaction of the different subunits of the reduced affinity reporter system (e.g., a previously determined known background level). As developed in more detail below, evaluation may include observing activity at two or more times during a given observation period, e.g., before and after contact of the cell with a test agent, etc., as may be required by a given assay protocol. This evaluation step may include providing a suitable substrate for the enzyme of the system; and detecting the enzyme mediated production of a detectable product therefrom, as developed in more detail below.

The reporter systems disclosed herein may be used to assay binding interactions of putative binding moieties attached to reporter subunits through complementation between the reporter subunits which produce a detectable signal. In addition to testing for direct binding interactions between the putative binding moieties, interactions dependent upon one or more additional molecules or ions may be evaluated. Further, multi-molecular interactions in living animal cells can be evaluated, as well as the influence of various drugs, peptides and pharmaceuticals on these interactions.

In one embodiment, the binding affinity of one or more putative binding moieties may be measured by providing a reporter system including one component having one of the moieties bound to a first reporter subunit and at least one other component including one other putative binding moiety bound to a second reporter subunit. The binding moieties may be different or the same. In the system, the reporter subunits are capable of binding and generating a detectable signal only if they are brought into proximity to one another, e.g., by the binding of the one or more putative binding moieties. The signal can be directly or indirectly detected and quantitated, e.g., by comparing the signal to a control value (e.g., obtained in a suitable control assay).

In one embodiment of the invention, protein-protein interactions can be detected and quantitated. The signal produced by the complementing reporter subunits can serve as an indicator of binding between the putative binding moieties, either directly or indirectly via a third substance. Signals which could be detected include light emission and absorbance. Exemplary signals include chromogenic, fluorescent and luminescent signals. These signals can be detected and quantitated visually or through the use of spectrophotometers, fluorimeters, microscopes, scintillation counters or other instrumentation known in the art.

Binding of components of the reporter systems disclosed herein will depend upon factors in solution, such as pH, ionic strength, concentration of components of the assay, and temperature. Assay solutions can be designed and developed for a particular system. The reporter systems disclosed herein can be used to conduct assays in solutions, such as buffered cell free solutions, cell interiors, solutions of cells, solutions of cell lysates, and solutions of cell fractions, such as nuclear fractions, cytoplasmic fractions, mitochondrial fractions, and membrane fractions. Methods for preparing assay solutions, such as enzyme assay solutions, cell extracts, and cell suspensions, known in the art may be used. For example, physiologically compatible buffers such as phosphate buffered saline may be used. See for example, the series, Methods in Enzymology, Academic Press, New York.

In one embodiment, the reporter subunits are capable of complementing one another to form an enzymatically active complex that is capable of catalyzing the conversion of a substrate to a product which is detectable, either directly or indirectly. In one embodiment, the reporter system can include two or more components, each of which is a fusion protein, wherein the fusion proteins each comprise a putative binding protein fused to a low affinity reporter subunit. Thus, nucleic acids encoding the fusion proteins can be constructed, introduced into cells and expressed in cells. Alternatively, the bound reporter units or bound binding moieties can be detecting by detecting the binding of a labeled specific binding moiety such as an antibody to the bound complex.

In one embodiment, the low affinity reporter subunits may be complementing subunits of β-gal, as reviewed above. The system may include three or more reporter subunits all of which are required to associate in order to produce the detectable signal. Methods for detecting the reaction products of active β-gal that have been developed in the art may be used. For example, β-galactosidase activity may be measured by a range of methods including live-cell flow cytometry and histochemical staining with the chromogenic substrate 5-bromo-4-chloro-3-indolyl β-D-galactopyranoside (X-Gal). Nolan et al., Proc. Natl. Acad. Sci, USA, 85:2603-2607 (1988); and Lojda, Z., Enzyme Histochemistry: A Laboratory Manual, Springer, Berlin, (1979). Histochemical staining for β-gal can be achieved by fixation of cells followed by exposure to X-gal.

Assays for β-gal activity as described in Mohler and Blau, Proc. Natl. Acad. Sci., 93:12423-12427 (1996), may be used. In one embodiment, intracellular analyses may be conducted by fixing cells and staining with the indigogenic substrate X-gal. Fixed cells also can be analyzed by assaying for β-gal activity by fluorescence histochemistry using an azo dye in combination with either X-gal or 5-bromo-6-chloro-3-indolyl β-D-galactopyranoside (5-6-X-Gal). A combination of interest is the azo dye red violet LB (Sigma Chemical, St. Louis, Mo.) and 5-6-X-Gal, referred to as Fluor-X-gal. For this combination, fluorescence micrographs can be obtained on a fluorescence microscope using a rhodamine/Texas Red filter set. Use of these substrates allows for β-gal-dependent fluorescence to be visualized simultaneously with two or more other fluorescent signals.

Vital substrates for β-gal, which can be used in living cells, are also encompassed by the invention. For example, a vital fluorogenic substrate, resorufin β-galactoside bis-aminopropyl polyethylene glycol 1900 (RGPEG) has been described. Minden (1996) BioTechniques 20(1):122-129. This compound can be delivered to cells by microinjection, electroporation or a variety of bulk-loading techniques. Once inside a cell, the substrate is unable to escape through the plasma membrane or by gap junctions. Another vital substrate that can be used in the practice of the invention is fluorescein di-β-D-galactopyranoside (FDG), which is especially well-suited for analysis by fluorescence-activated cell sorting (FACS) and flow cytometry. Nolan et al. (1988) Proc. Natl. Acad. Sci. USA 85:2603-2607 and Rotman et al. (1963) Proc. Natl. Acad. Sci. USA 50:1-6.

β-gal may also be detected using a chemiluminescence assay. For example, cells containing β-gal fusions are lysed in a mixture of buffers containing Galacton Plus substrate from a Galactolight Plus assay kit (Tropix, Bedford Mass.). Bronstein et al, J. Biolumin. Chemilumin., 4:99-111 (1989). After addition of Light Emission Accelerator solution, luminescence is measured in a luminometer or a scintillation counter.

Representative substrates that are suitable for spectrophotometric or fluorometric analysis include, but are not limited to: p-aminophenyl-β-D-galactopyranoside; 2'-N-(hexadecanol)-N-(amino-4'-nitrophenyl)-β-D-galactopyranoside; 4-methylumbel-liferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; m-nitrophenyl-β-D-galactopyranoside; p-nitrophenyl-β-D-galactopyranoside; and phenyl-β-D-galacto-pyranoside, 5-bromo-4-chloro-3-indolyl-β-D-galactopynanosiredse, resorufin-β-D-galacto-pyranoside, 7-hydroxy-4-trifluoromethyl coumarin, Ω-nitrostyryl-β-D-galactopyranoside, and flourescein-β-D-galactopyranoside. See, e.g., U.S. Pat. No. 5,444,161.

Reporter systems other than β-gal may also be used in the practice of the invention. For example, the enzyme β-glucuronidase (GUS) can be used as a reporter and chromogenic and fluorogenic GUS substrates have been developed. The GUS substrate 5-bromo-4-chloro-3-indolyl β-D-glucuronic acid (X-gluc) can be used in both chromogenic and fluorogenic applications, as follows. In one method of chromogenic staining, fixed cells are washed in PBS and stained with 2 mM X-gluc (Molecular Probes, Eugene Oreg.), 10 mM EDTA, 0.5 mM $K_3$ Fe(CN)$_6$, 0.5 mM $K_4$ Fe(CN)$_6$, 0.1% Triton X-100, 0.1 M NaPO$_4$. Fluorogenic staining may be achieved by using a combination of 5-bromo-6-chloro-3-indolyl β-D-glucuronic acid (5, 6 X-gluc, Molecular Probes, Eugene, Oreg.) and Fast Red Violet LB (Sigma Chemical, St. Louis, Mo.). Fixed cells are rinsed with PBS and stained in 50 µg/ml 5, 6 X-gluc and 100 µg/ml Fast Red Violet LB, then rinsed in PBS. Fluorescence is detected on a fluorescence microscope adjusted for detection of rhodamine fluorescence. In one embodiment of the invention, the reporter subunits include an enzyme and an inhibitor of the enzyme. In these embodiments, the inhibitor has a low affinity for the enzyme. In this case, association between the putative binding moieties is evidenced by inhibition of the activity of the enzyme. Exemplary enzymes include β-gal, GUS, β-lactamase, etc.

The methods disclosed herein enable the detection and quantitation of binding events in cell lysates, as well as in intact cells. Thus, interactions between fully folded proteins are detectable, and co-translational expression of the binding moieties is not necessary for binding to be detected.

In the practice of the invention, the reaction product may be detected indirectly, for example, through immunological techniques, such as immunofluorescent labeling.

Protein-protein interactions can be measured in a reporter system which includes one or more fusion proteins. The fusion proteins each include a putative binding protein coupled to a low affinity reporter subunit. For intracellular expression of the fusion proteins, one or more fusion gene constructs are prepared which include sequences encoding the fusion protein(s). The fusion gene constructs may be introduced into cells by methods available in the art, including, but not limited to, viral vectors, transformation, co-precipitation, electroporation, neutral or cationic liposome-mediated transfer, microinjection or gene gun.

A variety of cell-based assays can be conducted using the cells containing the fusion gene constructs. Binding of the putative binding moieties on the fusion proteins expressed in the cells can be confirmed by detecting the signal produced by the reporter subunits undergoing complementation mediated by the binding members. Thus, for example, when the reporter subunits are complementing β-gal subunits, cells exhibiting β-gal activity indicate binding between the putative binding moieties within those cells.

The fusion gene constructs may also contain promoters and other transcriptional and/or translational regulatory sequences that are normally associated with the gene encoding the putative binding moiety. This permits the study of physiologically-relevant levels of the putative binding proteins in vivo, in contrast to systems in which test proteins are overexpressed. Further, this permits the study of naturally-occurring changes in levels of binding activity over time and can reveal the effects of endogenous or exogenous substances on binding interactions.

The methods and compositions of the invention can also be used to study other molecules which influence the interaction of two putative binding partners, e.g., in screening assays, including high-throughput screening assays. Proteins, peptides, nucleic acids, carbohydrates, lipids, ions, small molecules, synthetic compounds or other substances (either endogenous to the cell or exogenously added) may act as either agonists or antagonists of a binding interaction. By measuring the effect of such molecules on, for example, β-gal activity produced by cells containing two or more fusions representing a particular pair of test proteins, agonist or antagonist activity of such molecules can be determined. Use of the methods and compositions of the invention will allow high-throughput assays to be carried out to test for agonists or antagonists of a particular binding interaction. Such high-throughput assays will be especially valuable in screening for drugs that influence medically-relevant protein-protein interactions.

Putative binding partners, or putative binding moieties, as used in the invention, can include molecules which do not normally interact with each other, but which each interact with a third molecule so that, in the presence of the third molecule, the putative binding partners are brought together. Thus, substances which influence an interaction between putative binding partners include those which stimulate a weak interaction between putative binding partners, as well as one or more molecules which mediate interaction between molecules which do not normally interact with each other. In addition, substances which influence an interaction between putative binding partners can include those which directly or indirectly affect an upstream event which results in association between the putative binding partners. For example, if phosphorylation of one of the putative binding partners endows it with the capacity to associate with another of the putative binding partners; substances which influence the interaction of the putative binding partners include those which directly or indirectly affect a kinase activity.

Assays can be developed as disclosed herein to examine the effect on intermolecular interactions of a variety of compositions including drugs such as antipyretic and anti-inflammatory drugs, analgesics, antiarthritics, antispasmodics, antidepressants, antipsychotics, tranquilizers, antianxiety drugs, narcotic antagonists, antiparkinsonism agents, cholinergic antagonists, chemotherapeutic agents, immunosuppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins.

Protein-protein interactions mediated by a third molecule can be detected and quantitated. The kinetics of binding also can be studied. For example, kinetics of binding can be determined by measuring β-gal activity at different times following addition of binding mediator to cultures of cells expressing fusions of first and second binding members and first and second reporter subunits. A dose-response curve can also be obtained, in which the extent of binding, as measured by β-gal activity, is determined as a function of binding mediator concentration. This assay can be adapted to control for the possible effect of a protein component on its fusion partner, thereby enabling the study of protein-protein interactions in a quantitative fashion. For example, tripartite fusion constructs including a reporter subunit, a binding protein and the protein of interest are provided. The absolute values of β-gal activity obtained by simple co-expression of a fusion containing a test protein of interest and fusions containing different potential interacting partners is determined. In parallel samples, β-gal activity is measured upon induction of complementation with a fixed amount of test protein. The ratio of β-gal activity obtained in the absence and the presence of test protein indicates the relative abilities of the different protein pairs to interact with each other. A further advantage of the tripartite fusion system is that the presence of the first and second binding member components provides a flexible hinge domain between the β-gal mutants and the test protein. This reduces the possibility of interference between the β-gal component and the test protein. Furthermore, it allows direct testing of the functional integrity of the β-gal components in the fusions without the need for reckoning into more efficient viral vectors.

The reporter system can also be designed with controls to permit the quantitation of the expression level of the β-gal fusion proteins. This will make it possible to control for potential differential expression of the two (or more) fusion proteins. For example, a peptide tag for which well-characterized monoclonal antibodies are available may be fused in frame at the C-terminus of each β-gal mutant. Different tags, such as flag, HA and myc may be used for the different subunits, to allow differential detection of the two mutants even when coexpressed in the same cells. In parallel with the determination of β-gal activity in the lysates of these cells, an ELISA assay can determine the precise amount of each β-gal fusion protein in the same lysates. First, a polyclonal anti-β-gal antiserum may be used to immobilize the antigens. Then the monoclonal antibody directed against the appropriate tag followed by an enzyme-linked anti-mouse secondary antibody may be used to quantify the amount of the β-gal fusion protein of interest. Such an approach, employing well-characterized techniques, should allow a determination of the expression levels of each fusion protein. This modification will be useful where the attached tag does not impair the binding of the protein or the ability of the reporter subunits to complement.

Utility

Embodiments of the invention can be used in a broad range of studies of multi-protein and other types of multi-molecular interaction to be carried out quantitatively or qualitatively in living cells. In what follows, non-limiting examples of different applications of the methods of the invention are provided.

The methods of the invention can be used to screen for new binding partner(s) for a given target protein. In this embodiment, the target protein, fused to a first reporter subunit, is stably expressed in a well-characterized cell line. Expression libraries containing cDNAs fused to a second reporter subunit are introduced into these cells using, for example, retroviral vectors (e.g., Kitamura et al., Proc Natl. Acad. Sci. USA 92:9146-9150 (1995)) or any other means of gene transfer known in the art. Vectors expressing gene products that interact with the target protein are isolated by identifying positive clones, i.e., clones that have activity resulting from complementation of the first and second reporter subunits. An advantage of this system is that the screen can be carried out in any cell type, regardless of the cell's milieu of endogenous (and potentially competing) proteins. In certain embodiments, the target protein is localized to a specific cellular compartment, with the aim of identifying proteins involved in interactions restricted to that particular location. The use of fluorescence-activated cell sorting techniques is particularly well-suited to this embodiment of the invention. For example, β-gal-positive cells which contain cDNAs expressing gene products that interact with the target protein will generate a signal that will allow such cells to be purified by cell-sorting techniques. Such cDNAs could be delivered, for example, using retroviral vectors that allow introduction of high complexity cDNA libraries with high infection efficiency.

The assays and methods of the invention can also be carried out in the presence of extracellular signaling molecules, growth factors or differentiation factors, peptides, drugs or synthetic analogs, or the like, whose presence or effects might alter the potential for interaction between two or more given proteins in a particular cell type.

Detection of molecular interactions, using the methods and compositions of the invention, is not limited to those occurring in the nucleus, nor is it limited to intracellular interactions. For instance, interactions involving surface receptors can be detected in the practice of the invention. In one embodiment, the invention provides new techniques for detecting ligand-induced dimerization of surface receptors in living cells. Dimerization, or higher order oligomerization, of cell surface receptors is often a prerequisite for receptor activation and ensuing signal transduction. The practice of the invention is not limited to detection of interaction between two different molecules. Multimerization of a molecule can also be detected using the methods and compositions of the invention.

In certain embodiments, the subject methods of the invention are employed with high-titer, high-complexity cDNA libraries in retroviruses to identify interaction partners of a specific test protein in mammalian cells (e.g., to perform functional genomics at the protein level). For this application, construction of cDNA libraries in retroviral vectors wherein the cDNA coding sequence is fused to a sequence encoding a first reporter subunit will be used, e.g., where it is present in a first retroviral vector. In a second series of retroviral vectors, a second reporter subunit will be fused to a variety of different proteins that will be tested for their ability to bind to the protein of interest. Testing will be conducted by co-infection of cells with the first and one of the series of second retroviral vectors. Those test proteins which are capable of binding to the protein of interest will allow detection of a reporter signal in cells in which they are co-expressed with the protein of interest. This application is also useful in screening for agonists and antagonists of medically-relevant protein interactions.

In one embodiment of the invention, cells in which a protein encoded by one of the series of second vectors is able to interact with the binding protein of interest encoded by the first vector are detected and isolated by flow cytometry or fluorescence-activated cell sorting (FACS). Methods for flow cytometry and FACS are well-known in the art; e.g., Nolan et al. (1988) Proc. Natl. Acad. Sci. USA 85:2603-2607; Webster et al., Exp. Cell Research, 174:252-265 (1988); and Parks et al. (1986) in The Handbook of Experimental Immunology, (eds. Weir, D. M., Herzenberg, L. A., Blackwell, C. C. & Herzenberg, L. A.), Blackwell, Edinburgh, 4th edition, pp. 29.1-29.21. In this way, clones of cells in which binding occurs can be isolated and propagated for further study. This aspect is particularly suited for studies of developmental mechanisms, wherein it is possible to select a population of cells in which a particular developmentally-relevant interaction has occurred and study the further development of that cell population, while at the same time, studying the further development of cells in which the interaction has not occurred, for comparison. In a similar fashion, the practice of the invention makes it possible to isolate and/or study the further development of cells exhibiting interactions involving protein such as transcriptional regulatory proteins, translational regulatory proteins, DNA replication proteins, mRNA splicing proteins, proteins involved in signal transduction, proteins involved in cell-cell and cell-substrate adhesion (for example, cell movement, axon guidance and angiogenesis), oncogene products, tumor suppressors, proteins involved in cell-cycle control and viral proteins, such as those involved in regulation of viral replication, virus-host interactions and virus assembly, and proteins which are subunits, crosslinkers, modifying agents or molecular motors within the cytoskeleton of cells.

For a given target protein whose gene is capable of being fused to a reporter subunit, it is possible to identify known and heretofore unknown proteins or other endogenous or extraneous substances with which it interacts, by using the compositions and methods of the invention. In like manner, for a sequence which encodes a protein of unknown function, such as may be obtained from a nucleic acid sequence database, (or a plurality of sequences such as a cDNA library) the practice of the invention allows one to identify molecules with which the encoded protein interacts. The identity of the interacting molecule(s) provides information with respect to the structure and/or function of the unknown protein. As such, embodiments of the invention aid in the identification and characterization of newly-discovered proteins and protein-coding nucleic acid sequences.

In another aspect of the invention, a shotgun approach to the identification of protein-protein interactions can be taken by generating a first set of constructs which will express the encoded products of one cDNA library fused to a first reporter subunit and a second set of constructs which will express the encoded products of a second (or the same) cDNA library, fused to a second reporter subunit. Co-expression of the two sets of constructs and selection of cells in which complementation occurs allows the isolation of clones and the identification of cDNAs which encode interacting partners. One or both of the interacting partners may be known; alternatively, both of the interacting partners may represent heretofore unidentified proteins. If both partners are known, new information about their binding specificity may be obtained. If one partner is known, it may provide information on the function of the unknown binding partner. If neither are known, the observation that they interact may assist in the eventual identification of one or both of the interacting pair.

The invention may be applied to studies of the mechanisms that regulate either homo- or hetero-dimerization or multimerization of specific molecules, including high efficiency screening to identify synthetic or naturally occurring compounds capable of influencing such dimerization/multimerization.

The invention may be applied to studies of abnormal or pathologic protein aggregates found in central nervous system diseases, e.g., Parkinson's, Alzheimer's, Cruzsfeld-Jacob, etc. These studies may be performed in in vivo or in vitro model systems. In in vitro assays, a number of cell types may be employed, ranging from cultured neuronal cells (e.g., mammalian, insect, C. elegans, etc.) to non neuronal cells that are engineered to express the protein aggregates of interest.

For example, recent studies have employed yeast cells to study α-synuclein misfolding and aggregation which is associated with neurodegenerative disorders, including Parkinson's disease (see, e.g., Cooper et al. 2006 Science 313:324-8, incorporated herein by reference). In accordance with the description of the present invention above, a yeast cell that inducibly expresses two fusion proteins of α-synuclein, each with a corresponding reporter subunit, is produced. When α-synuclein aggregation occurs in these cells (i.e., when both fusion proteins are expressed), the reporter subunits will complement one another to generate a functional enzyme having a detectable activity. In performing screening assays, the expression of both α-synuclein fusion proteins is induced in the yeast cells in the presence or absence of one or more candidate agents (where the agents may be added before, during, or after induction of α-synuclein expression). Agents that inhibit, prevent and/or reverse α-synuclein aggregation in the cells will have reduced reporter gene activity as compared to control cells. Agents having this desirable activity are further assessed for their suitability as therapeutics for treating disease conditions caused by α-synuclein aggregation.

As indicated above, other proteins (or combinations of proteins) that form pathological aggregates in cells may be the subject of the screening assay described above. These assays are very useful in therapeutic agent screens because they are rapid and amenable to high throughput screening (HTS) applications (e.g., high throughput flow cytometric screening).

The present invention also finds use in assays in which the presence of transient or unstable protein/protein interactions in a cell is being determined. Because the present invention enables readout of protein/protein association in a cell in vivo, they can be employed to detect unstable or transient protein/protein interactions where standard cellular fractionation assays cannot (i.e., due to disruption of the protein/protein interaction during processing of the sample prior to detection).

For example, the present invention can be employed to study heat shock protein (HSP, e.g., HSP-90) chaperone complex formation in a variety of cell types, including yeast, insect, mammalian, plant, etc. (see, e.g., Queitsch et al. 2002 Nature 417:618; Cowen and Lindquist, 2005 Science 309: 2185; and Rutherford and Lindquist 1998 Nature 396:336; each of which is incorporated herein by reference). In these assays, an HSP/reporter subunit fusion protein and a corresponding target protein/reporter subunit fusion protein are constructed and expressed in a cell. The cells, either in vitro or in an organism (e.g., a transgenic animal) are subjected to one or more conditions of interest (e.g., drug/antibiotic treatment, temperature stress, oxidative stress, nutrient stress, treated with cytokine/hormone/growth factor(s), etc.) and the protein/protein interaction of the HSP fusion protein and the target fusion protein is monitored (i.e., formation and dissolution of the complexes is monitored). A screen can also be set up in which a reporter fusion library (e.g., a nucleic acid library) is tested for the presence of HSP-associating members under specific conditions. For example, cells expressing an HSP fusion protein and a library fusion protein (e.g., expressing a protein encoded by a nucleic acid from the library) can be treated with drug and/or under a specific condition and the association/dissociation of HSP with the library protein assayed. Such assays find use in determining how the activity of proteins, both wild type and mutant forms, are regulated under distinct conditions.

The invention can be used for investigations relating to the localization of specific complexes within intact cells, or intact animals. Types of cells which can be used are primary or established cell lines and other types of embryonic, neonatal or adult cells, or transformed cells (for example, spontaneously- or virally-transformed). These include, but are not limited to fibroblasts, macrophages, myoblasts, osteoclasts, osteoclasts, hematopoietic cells, neurons, glial cells, primary B- and T-cells, B- and T-cell lines, chondrocytes, keratinocytes, adipocytes and hepatocytes.

It is also possible, through practice of the invention, to devise systems for regulation of enzyme activity by regulating the association of complementing mutants. This aspect of the invention has potential applications to human therapy, as a method to regulate the enzyme-driven conversion of prodrugs into their active forms.

Processes involving molecular interactions, particularly protein-protein interactions, which can be studied in the practice of the invention include, but are not limited to, transcription, translation, replication, mitosis, growth control, progression and regulation of the cell-cycle, apoptosis, cell-cell, cell-substratum and cell-ligand interactions, intracellular signal transduction cascades, oncogenesis, cell lineages, and embryonic development. Examples of cell ligands include leptin and growth factors such as epidermal growth factor (EGF), nerve growth factor (NGF), platelet-derived growth factor (PDGF), and insulin-like growth factors I and II (IGF-I and IGF-II), transforming growth factors α and β (TGF-α and TGF-β), endorphins and endorphin receptors, prostaglandins and their receptors, cytokines and their receptors, neurotransmitters and their receptors, adrenergic receptors, and cholinergic receptors. Receptors which could interact with ligands include, but are not limited to: EGF, NGF, and PDGF receptors and leptin receptors.

Additional interactions that can be studied by the practice of the invention include interactions involved in cell metabolism and cell structure. These include, but are not limited to, interactions that are involved in energy metabolism or which establish or modify the structure of the membranes, cytoplasm, cytoskeleton, organelles, nuclei, nuclear matrix or chromosomes of cells. Interactions among constituents of the extracellular matrix, or between constituents of the extracellular matrix and cells, can also be studied with the methods and compositions of the invention.

Additional utilities of the subject reduced affinity enzyme complementation reporter systems include, but are not limited to, those described in Published U.S. Patent Application Serial Nos. 20030219848; as well as in U.S. Pat. Nos. 4,378, 428; 4,708,929; 5,037,735; 5,106,950; 5,362,625; 5,464,747; 5,604,091; 5,643,734; and PCT application nos. WO96/19732; WO98/06648; WO92/03559; WO01/0214; WO01/60840 and WO 00/039348; the disclosures of which are herein incorporated by reference.

Kits

Also provided by the subject invention are kits for use in practicing one or more of the above described applications. In certain embodiments, kits at least include a cell that expresses, either constitutively or inducibly, one or more fusion proteins that include a binding member and a reporter subunit, as reviewed above. In certain embodiments, kits include elements for making such cells, e.g., first and second nucleic acids encoding first and second fusion proteins present on the same or different vectors and/or nucleic acids encoding reporter subunits to which proteins of interest can be fused using standard molecular biology techniques, as reviewed above. The kits may further include one or more additional components which find use in practicing embodiments of the invention, including but not limited to, enzyme substrates, cell growth media, etc.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Reduced Affinity β-galactosidase System

We recently described a proximity-based low affinity enzyme complementation system for monitoring protein translocation using β-gal. To achieve low affinity complementation, the classic α peptide first described by Jacob and Monod (1961) was truncated and mutated at specific residues based on the crystal structure in order to derive the α peptide ($\alpha^*$) that weakly complements the omega (ω) fragment. Truncations past amino acids 49 result in a 10-fold decrease in β-galactosidase activity. To assay protein movement, one enzyme fragment, ω, was localized in a particular subcellular region and the small complementing $\alpha^*$ peptide was fused to the protein of interest. The concentration of $\alpha^*$ in the immediate vicinity of ω correlated with the amount of enzyme activity obtained in a dose- and time-dependent manner, serving as a genetically encoded biosensor for local protein concentration (T. S. Wehrman, C. L. Casipit, N. M. Gewertz, H. M. Blau, Nat Methods 2, 521 (July, 2005)). Due to their low affinity, the interaction of the $\alpha^*$ and ωβ-gal fragments is not sufficiently strong to maintain a complemented enzyme. As a result, the β-gal activity obtained at any given time is a measure of the dynamic interaction of the two fragments, a reflection of their local concentration. This reduced affinity system is further described in U.S. application Ser. No. 11/132,764 filed on May 18, 2005, the disclosure of which system and its method of product as described in the experimental section of that application is herein incorporated by reference. The Ser. No. 11/132,764 application sets forth and shows in FIG. 1 thereof a wild type N terminal β-galactosidase sequence, namely MGVITDSLAVVLQRRDWENPGVTQLN RLAAHPPF ASWRNSEEAR TDRPSQQLR, (SEQ ID NO: 7).

Using this system the interaction of two proteins is measured as a function of complementation of low affinity mutant subunits of the β-galactosidase (β-gal) enzyme fused to the receptor proteins (FIG. 1A). Inducible and reversible interactions can be assayed, the signal to noise ratio is high, and receptor homo- and heterodimers can be compared in a quantitative manner in the plasma membranes of large polyclonal cell populations.

This combination of features is not found in other protein interaction detection systems based on energy transfer (Y. Xu, D. W. Piston, C. H. Johnson, Proc Natl Acad Sci USA 96, 151 (Jan. 5, 1999); B. A. Pollok, R. Heim, Trends Cell Biol 9, 57 (February, 1999)) or split enzymes including dihydrofolate reductase (J. N. Pelletier, F. X. Campbell-Valois, S. W. Michnick, Proc Natl Acad Sci USA 95, 12141 (Oct. 13, 1998)), β-lactamase (A. Galarneau, M. Primeau, L. E. Trudeau, S. W. Michnick, Nat Biotechnol 20, 619 (June, 2002); T. Wehrman, B. Kleaveland, J. H. Her, R. F. Balint, H. M. Blau, Proc Natl Acad Sci USA 99, 3469 (Mar. 19, 2002)), luciferase (R. Paulmurugan, S. S. Gambhir, Anal Chem 75, 1584 (Apr. 1, 2003)), and the previously described β-galactosidase (F. Rossi, C. A. Charlton, H. M. Blau, Proc Natl Acad Sci USA 94, 8405 (Aug. 5, 1997); F. Rossi, C. A. Charlton, H. M. Blau, Proc Natl Acad Sci USA 94, 8405 (Aug. 5, 1997)). This new reduced-affinity β-galactosidase system enables a comparative analysis of the combinatorial interactions of the ErbB family members associated with breast cancer, as reviewed immediately below.

II. Use of Reduced Affinity β-galactosidase System to Investigate the Capacity of the EGFR, ErbB2 and ErbB3 to Homo and Heterodimerize ErbB2 (HER2/Neu), a member of the ErbB family of receptor tyrosine kinases, is overexpressed in 30% of breast cancers and most clearly associated with a malignant phenotype and poor prognosis, especially if co-expressed with the Epidermal Growth Factor Receptor (EGFR) (D. J. Slamon et al., Science 235, 177 (Jan. 9, 1987); D. Gschwantler-Kaulich et al., Oncol Rep 14, 305 (August, 2005): M. P. DiGiovanna et al., J Clin Oncol 23, 1152 (Feb. 20, 2005)). For breast cancer patients whose tumors overexpress ErbB2, the monoclonal antibody Herceptin has revolutionized treatment by extending lifespan and decreasing recurrence rate in an unprecedented manner (M. J. Piccart-Gebhart et al., N Engl J Med 353, 1659 (Oct. 20, 2005); M. A. Cobleigh et al., J Clin Oncol 17, 2639 (September, 1999); E. H. Romond et al., N Engl J Med 353, 1673 (Oct. 20, 2005)). However, Herceptin is only effective in a subset of cases in which it is used, and to date there is no accepted basis for predicting which ErbB2 positive tumors will respond to treatment. This is, in part, due to an incomplete understanding of the mechanism by which Herceptin acts. Although there is some evidence that Herceptin targets tumor cells for destruction by the immune system (R. A. Clynes, T. L. Towers, L. G. Presta, J. V. Ravetch, Nat Med 6, 443 (April, 2000)), the antibody was originally selected as an inhibitor of tumor cell growth in vitro independent of an immune response (R. M. Hudziak et al., Mol Cell Biol 9, 1165 (March, 1989)). Herceptin is not known to block the formation of heterodimers of ErbB2, yet its inhibitory effects on cell proliferation suggest that it interferes with signal transduction by the ErbB family of tyrosine kinases. One reason that the mechanism of action of Herceptin has remained elusive is the difficulty in monitoring the interactions of the ErbB receptors in a quantitative manner using available biochemical methods, including purified or co-immunoprecipitated receptors (K. M. Ferguson, P. J. Darling, M. J. Mohan, T. L. Macatee, M. A. Lemmon, Embo J 19, 4632 (Sep. 1, 2000); T. Horan et al., J Biol Chem 270, 24604 (Oct. 13, 1995); D. Karunagaran et al., Embo J 15, 254 (Jan. 15, 1996).

Here we investigated the capacity of the EGFR, ErbB2 and ErbB3 to homo and heterodimerize using a novel protein interaction detection system that allows receptor interactions to be monitored in the membranes of intact cells, as described in section I above. Using this system the interaction of two proteins is measured as a function of complementation of low affinity mutant subunits of the β-galactosidase (β-gal) enzyme fused to the receptor proteins (FIG. 1A). Inducible and reversible interactions can be assayed, the signal to noise ratio is high, and receptor homo- and heterodimers can be compared in a quantitative manner in the plasma membranes of large polyclonal cell populations. This combination of features is not found in other protein interaction detection systems based on energy transfer (Y. Xu, D. W. Piston, C. H. Johnson, Proc Natl Acad Sci USA 96, 151 (Jan. 5, 1999); B. A. Pollok, R. Heim, Trends Cell Biol 9, 57 (February, 1999)) or split enzymes including dihydrofolate reductase (J. N. Pelletier, F. X. Campbell-Valois, S. W. Michnick, Proc Natl Acad Sci USA 95, 12141 (Oct. 13, 1998)), β-lactamase (A. Galarneau, M. Primeau, L. E. Trudeau, S. W. Michnick, Nat Biotechnol 20, 619 (June, 2002); T. Wehrman, B. Kleaveland, J. H. Her, R. F. Balint, H. M. Blau, Proc Natl Acad Sci USA 99, 3469 (Mar. 19, 2002)), luciferase (R. Paulmurugan, S. S. Gambhir, Anal Chem 75, 1584 (Apr. 1, 2003)), and the previously described β-galactosidase (F. Rossi, C. A. Charlton, H. M. Blau, Proc Natl Acad Sci USA 94, 8405 (Aug. 5, 1997); F. Rossi, C. A. Charlton, H. M. Blau, Proc Natl Acad Sci USA 94, 8405 (Aug. 5, 1997)). We postulated that a new β-galactosidase system that we developed for assays of protein translocation (T. S. Wehrman, C. L. Casipit, N. M. Gewertz, H. M. Blau, Nat Methods 2, 521 (July, 2005)), could enable a comparative analysis of the combinatorial interactions of the ErbB family members associated with breast cancer.

For the proposed studies of the interactions of the ErbB family of receptors, the potential of the proximity based low affinity β-gal complementation system for analyzing specific inducible protein-protein interactions was initially validated. First, the rapamycin inducible interaction of FKBP12 and FRB, cytoplasmic proteins that associate with high affinity (J. Chen, X. F. Zheng, E. J. Brown, S. L. Schreiber, Proc Natl Acad Sci USA 92, 4947 (May 23, 1995)), was assayed by chemiluminescence. Treatment of cells expressing FKBP12ω and FRBα* with rapamycin for two hours resulted in a 10-fold increase in β-gal activity (FIG. 1B). To determine whether the β-gal system could also be used to monitor the interaction of lower affinity, reversible interactions, the association of the G-protein coupled receptor, the β2adenergic receptor (B2AR) with β-arrestin2 was evaluated. Upon stimulation, B2AR becomes phosphorylated and binds β-arrestin2. Treatment of cells expressing the B2AR-ω and β-arrestin2α* fusion proteins with agonist (isoproterenol) resulted in a 5-fold increase in enzyme activity, which was prevented by pretreatment with the antagonist (propranolol) (FIG. 1C-E). The dose-response and EC50 obtained as a function of β-gal activity are in good agreement with published values (R. H. Oakley et al., Assay Drug Dev Technol 1, 21 (November, 2002)), indicating that low affinity proximity based α-complementation can be used as a quantitative measure of protein-protein interactions in their natural context, the membranes of intact cells.

ErbB2 is generally regarded as the preferred heterodimerization partner for each of the ligand bound ErbB receptors, EGFR and ErbB3 (D. Graus-Porta, R. R. Beerli, J. M. Daly, N. E. Hynes, Embo J 16, 1647 (Apr. 1, 1997)), however, the characterization of ErbB2 interactions using conventional methods has been problematic. For example, the extracellular domain of ErbB2 has not been shown to form heterodimers in solution (K. M. Ferguson, P. J. Darling, M. J. Mohan, T. L. Macatee, M. A. Lemmon, Embo J 19, 4632 (Sep. 1, 2000)), and the use of phosphorylation as a surrogate marker for receptor interactions has led to conflicting results (D. J. Riese, 2nd, T. M. van Raaij, G. D. Plowman, G. C. Andrews, D. F. Stern, Mol Cell Biol 15, 5770 (October, 1995); D. Graus-Porta, R. R. Beerli, J. M. Daly, N. E. Hynes, Embo J 16, 1647 (Apr. 1, 1997)). We applied the low affinity β-gal system to studies of the EGFR, ErbB2 and ErbB3 in the plasma membrane. To prevent receptor clustering and internalization, the intracellular domains of the receptors were not included in the receptor-α* or receptor-ω chimeras (FIG. 1F). Exposure to EGF resulted in a time-dependent increase in enzyme activity, demonstrating that the extracellular and transmembrane domains of these receptors are sufficient to mediate heterodimerization (FIG. 1G). To verify that the β-gal assay could monitor the dynamic nature of this interaction, experiments were performed in which the inducers, EGF and TGF-α, were first added and then removed from the media prior to analysis. β-gal activity decreased over time and the signal decayed more rapidly following TGF-α than after EGF exposure, indicating that the rate of loss of β-gal activity exhibits ligand-specificity (FIG. 1H). These results show that the β-gal assay can monitor reversible interactions, unlike other enzyme complementation systems described to date.

To perform a quantitative comparison of the different pairs of receptors, receptor expression level in cells was controlled, as the amount of β-gal fusion protein affects β-gal enzyme activity (FIG. 2). To this end, two parental cell lines were constructed using C2C12 cells in which ErbB family members are expressed at very low levels (S. Corti et al., Exp Cell Res 268, 36 (Aug. 1, 2001)). These cells were engineered to express either the ErbB2-ω or the EGFR-ω fusion proteins. Each of the ω-expressing parental cell lines were then split and transduced with each of three constructs encoding different α-fusion proteins, EGFR-α*, ErbB2-α*, and ErbB3-α*. Because the cells were generated from the same parental line, they expressed equivalent amounts of ω. To allow measurement of α* chimeric protein expression levels, YFP was included in each construct, between the ErbB receptor and the α*. Cells expressing similar YFP levels were isolated by FACS so that the levels of α*-fusion proteins were comparable. YFP was imaged by confocal microscopy to ensure that the receptor fusion proteins were appropriately localized to the plasma membrane, which is essential to their function (FIG. 3).

Ligand stimulated enzyme activities were assessed for each of the six cell lines expressing pairs of receptors. Cells were exposed either to the ligand EGF that binds the EGFR or to the ligand heregulin (HRGβ1) that binds the ErbB3 receptor (N. E. Hynes, H. A. Lane, Nat Rev Cancer 5, 341 (May, 2005)). All of the expected interactions were observed (FIG. 4A). EGF led to homodimerization of the EGFR and heterodimerization of EGFR with ErbB2, whereas HRGβ1 failed to induce interaction of these receptors. When cells were compared that expressed EGFRω-ErbB2α* or ErbB2ω-EGFRα*, the responses were similar. This finding was important, as it indicated that similar interactions occurred irrespective of whether the receptors were fused to α* or ω. Although the phosphorylation of ErbB3 by the EGFR has been shown by others (D. J. Riese, 2nd, T. M. van Raaij, G. D. Plowman, G. C. Andrews, D. F. Stern, Mol Cell Biol 15, 5770 (October, 1995); K. Zhang et al., J Biol Chem 271, 3884 (Feb. 16, 1996)), we detected no significant interaction between these two proteins, indicating that activation of ErbB3 by the EGFR is unlikely to be mediated by dimerization of their-extracellular domains. The cells expressing ErbB2ω and ErbB3α* generated heterodimers only in response to HRGβ1, but not to EGF. The cells expressing ErbB2ω and ErbB2α* were not responsive to either EGF or HRGβ1 treatment consistent with the inability of ErbB2 to bind any known ligand.

The crystal structure of ErbB2 has revealed that it is in a constitutively active conformation, suggesting that it could spontaneously homodimerize and signal (H. S. Cho et al., Nature 421, 756 (Feb. 13, 2003); T. P. Garrett et al., Mol Cell 11, 495 (February, 2003)). However, this view is not supported by the observation that full activation of ErbB2 does not occur with ErbB2 alone but requires the presence of other ErbB receptors in the cell (Y. Yarden, Oncology 61 Suppl 2, 1 (2001)). In addition, biochemical studies have failed to detect ErbB2 homodimers in vitro. Our studies confirm that ErbB2 does not form spontaneous homodimers more readily than the other receptor pairs tested, since the enzyme activity is similar for all cell lines in the absence of inducer (FIG. 4B).

Three monoclonal antibodies against ErbB2 were tested for their effects on ErbB receptor dimer levels (FIG. 5A). Antibody L87 binds the extracellular domain of ErbB2, but has no effect on receptor activation (L. N. Klapper et al., Oncogene 14, 2099 (May 1, 1997)). When assayed by β-gal complementation L87 had no effect on the interaction of ErbB2 with either EGFR or ErbB3. Antibody 2C4 was found to prevent dimerization of ErbB2 with either ErbB3 or EGFR, in good agreement with previous reports in which activity was assayed as a function of phosphorylation (D. B. Agus et al., Cancer Cell 2, 127 (August, 2002)). Notably, Herceptin markedly inhibited the interaction of EGFRω with ErbB2α*. By contrast with 2C4, Herceptin exhibited relatively little inhibition of ErbB2ω-ErbB3α* dimerization. These effects of Herceptin were dose-dependent and inhibition of the EGFRω-ErbB2α* interaction occurred at doses on a par with 2C4 (FIG. 5B,C). To confirm that the results were not affected by the β-gal fragment to which the receptors were-fused, the same experiment was performed with EGFRα* and ErbB2ω and similar results were obtained (FIG. 6). We postulate that the greater inhibition of dimer formation by 2C4 is due to the fact that Herceptin binds the juxtamembrane domain of ErbB2, whereas 2C4 binds the dimerization arm of ErbB2.

The dimerization studies above indicate that Herceptin primarily inhibits the formation of ErbB2-EGFR heterodimers. Although it is possible that Herceptin inhibits the formation of ErbB2-EGFR heterodimers more strongly than ErbB2-ErbB3 heterodimers, this seems unlikely as the extracellular domains of ErbB receptors are highly homologous, both at the sequence and structural level. We postulate that since the EGFR readily homodimerizes, whereas ErbB3 does not (M. B. Berger, J. M. Mendrola, M. A. Lemmon, FEBS Lett 569, 332 (Jul. 2, 2004)), the propensity of the EGFR monomers to form homodimers is in competition with the formation of ErbB2-EGFR heterodimers. By contrast ErbB3 cannot homodimerize, leaving ErbB3 monomers available to heterodimerize with ErbB2, even in the presence of Herceptin. As a result, unlike ErbB3, EGFR would be progressively sequestered in EGFR-EGFR complexes becoming increasingly unavailable for heterodimerization.

Our data together with the known properties of the ErbB receptors, prompted us to test whether Herceptin impacted EGFR homodimerization in cells expressing both the EGFR and ErbB2. ErbB2 heterodimers and EGFR homodimers form with equal efficiency, as shown in FIG. 4A. As a result, inhibition of heterodimer formation by Herceptin treatment should result in a higher proportion of homodimers (B. S. Hendriks, H. S. Wiley, D. Lauffenburger, Biophys J 85, 2732 (October, 2003)). As a test of this hypothesis, the wildtype ErbB2 lacking a β-gal fragment was overexpressed in the EGFRα*-EGFRω cell line. As expected, exposure to EGF failed to stimulate β-gal activity, given the strong propensity for heterodimer formation (FIG. 7A). However, when the cells were preincubated with the Herceptin antibody, EGF caused an increase in β-gal activity, as the ErbB2 bound to Herceptin had diminished ability to heterodimerize with the EGFR. This disruption allowed EGFRα* and EGFRω to interact and homodimerize. Addition of 2C4 restored the EGF-induced increase in β-gal activity of the cell line to a greater extent, as expected given the more potent inhibition of ErbB2 heterodimers relative to Herceptin.

We reasoned that the increase in EGFR homodimer formation in the presence of Herceptin would result in a decrease of EGFR at the cell surface as the EGFR is rapidly internalized and degraded as a homodimer, but not as a heterodimer with ErbB2 (Z. Wang, L. Zhang, T. K. Yeung, X. Chen, Mol Biol Cell 10, 1621 (May, 1999)). To test this hypothesis, the wildtype EGFR and wildtype ErbB2 were co-expressed in cells and EGFR on the cell surface was quantitated by flow cytometry (FIG. 7B). Both Herceptin and 2C4 resulted in a rapid loss of EGFR from the cell surface upon EGF treatment by comparison with controls. Similar experiments were performed with the SKBR3 breast cancer cell line, that is known to overexpress both EGFR and ErbB2, exhibited a similar increase in EGF induced EGFR internalization in the presence of Herceptin and 2C4 (FIG. 7C). These experiments show that blocking heterodimerization of the EGFR and ErbB2 with Herceptin would not only lead to reduced ErbB2 activation, but also increased EGFR homodimer formation followed by more efficient downregulation of activated receptors. Together, these findings provide an explanation of the ability of Herceptin to inhibit the growth of ErbB2 expressing cancer cells.

The development of a method for monitoring dynamic receptor interactions in an intact membrane was pivotal to the study of the combinatorial interactions of the ErbB family members. This assay measures the interaction of proteins as a function of the enzyme activity generated upon induced proximity of the β-gal enzyme fragments to which they are fused. By controlling the expression levels of each fragment, the entire profile of receptor heterodimers and homodimers could be compared across cell lines expressing different receptor combinations. The assay is sensitive, quantitative, inducible and reversible. Although applied to ErbB family interactions in this study, the protein interaction detection system described here is readily adaptable to other protein interactions of interest.

Although Herceptin has been used clinically for more than a decade, there has been no clear characterization of its effect on ErbB family dimerization. We show here that Herceptin primarily impacts ErbB2-EGFR heterodimer levels, not ErbB2-ErbB3. As a result, Herceptin exposure should inhibit signaling by two interrelated mechanisms: (1) disruption of ErbB2-EGFR heterodimers and (2) reduction of total EGFR expression on the cell surface. Herceptin directly blocks the first, leading to an increase in EGFR homodimerization, followed by rapid internalization and ultimately a reduction in EGFR levels. Taken together, the findings in this study suggest a mechanism by which Herceptin inhibits ErbB receptor signaling and therefore tumor cell growth: targeting the ErbB2-EGFR heterodimer.

Importantly, the in vitro findings reported here correlate well with the recently reported ErbB2 receptor expression profiles of tumor samples from responders and non-responders to Herceptin. In patients whose tumors overexpress ErbB2, a response to Herceptin treatment is correlated with coexpression of the EGFR and its ligand, as opposed to ErbB3 (G. Hudelist et al., Int J Cancer (Sep. 13, 2005); B. L. Smith et al., Br J Cancer 91, 1190 (Sep. 13, 2004)). Thus, the data in this study provide a mechanistic basis for predicting a response and selecting patients who are likely to benefit from Herceptin therapy.

III. Materials and Methods

A. Generation of β-galactosidase fusion Proteins

The extracellular and transmembrane domains of EGFR (aa 1-679), ErbB2 (aa 1-686), and ErbB3 (aa 1-693) and full length B2AR (all human) were PCR amplified from cDNA clones with 5' MfeI and 3' XhoI sites. The PCR products were fused to the amino-terminus of the ω fragment in a WZL retroviral construct, and the YFPH31Rα (α*) retroviral constructs. The full coding sequence of human β-arrestin2 was PCR amplified from a cDNA clone and inserted into the MfeI-XhoI sites of the ω and α* vectors using primers containing EcoRI and XhoI sites. The complete coding sequence of FKBP12 and aa 2025-2114 of human FRAP were PCR amplified and inserted into the ω and α* vectors as MfeI-XhoI fragments. The full length ErbB2 and EGFR were also PCR amplified from a cDNA clone and inserted into an MFG retroviral vector using MfeI-XhoI restriction enzymes.

B. Virus Production and Cell Culture

Retroviral vectors were transfected into the Φnx-packaging cell line (P. L. Achacoso and G. P. Nolan) using lipofectamine 2000 transfection reagent (Invitrogen, Carlsbad Calif.) in 6-well dishes according to manufacturers instructions. 24 hours post transfection the viral supernatant was filtered through a 0.45 μm syringe filter onto C2C12 cells. Polybrene was added at a final concentration of 4 μg/ml and the plates spun at 1900 RPM in a Beckman tabletop centrifuge for 30 min. Cells were returned to a 37° C. 5% $CO_2$ humidifed incubator for 12 hours then the media was exchanged with fresh media. C2C12 cells were grown in 20% FBS DMEM containing pen/strep. When appropriate cells were selected with 1 μg/ml G418 (Invitrogen), or sorted for YFP expression on a FACSTAR flow cytometer using the FL1 channel. SKBR3 cell line was obtained from ATCC. The SKBR3 cells were cultured in McCoy's 5A medium supplemented with 10% FBS, pen/strep, and glutamine.

C. Cell Treatments and Assays

Herceptin and 2C4 were generous gifts from Genentech (Sliwkowski, M X). All other antibodies were obtained from Neomarkers, (Labvision). Recombinant human hEGF, hHRGβ1, and hTGF-α were obtained from Peprotech, resuspended in water and immediately frozen in aliquots. Isoproterenol, propranolol and rapamycin were from Sigma. Isoproterenol was resuspended in water prior to each experiment. For measurements of β-galactosidase activity cells were seeded at 20,000 cells/well of a 96-well dish overnight. After the appropriate treatment, media was removed from the cells and 50 μl Buffer B mixed with a 1:20 dilution of Galacton-Star (Gal-screen kit, Applied Biosystems) was added. Cells were incubated at RT for 45 min. before luminescence was measured in a Tropix TR717 luminometer with an integration time of 1 second. For the internalization assays, cells were seeded into 12-well dishes at least 24 hours prior to assay. Cells were serum starved for 4 hours in appropriate medium with no serum, then treated with 100 ng/ml EGF. The wells were trypsinized and placed on ice to prevent further endocytosis. Cells were rinsed in ice-cold medium, then stained in a 5% BSA/PBS solution using anti-EGFR Ab-11 (Neomarkers) conjugated to Alexa 647 (molecular probes) for 20 min. and washed again in 5% BSA/PBS. Antibody conjugation was performed according to manufacturer's instructions and used at the optimal titration.

As such, the present invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining whether a first and second protein interact by binding to each other, said method comprising:
   (a) providing a mammalian cell comprising:
      (i) a first fusion protein of said first protein and a first β-galactosidase fragment of a full length β-galactosidase enzyme, wherein said first β-galactosidase fragment is a variant minimal N-terminal β-galactosidase peptide about 60 amino acids or less in length; and
      (ii) a second fusion protein of said second protein and a second β-galactosidase fragment including greater than 60% of the full-length β-galactosidase enzyme;
   wherein said first and second β-galactosidase fragments have an affinity for each other which provides a known level of β-galactosidase activity in the absence of an interaction between said first and second proteins that is lower than the activity observed in the presence of an interaction between said first and second proteins, wherein said variant minimal N-terminal β-galactosidase peptide comprises a point mutation, insertion or deletion between amino acid residues 29 to 41, or a truncation terminating between amino acid residues 48 and 43, as set forth in a β-galactosidase peptide sequence according to SEQ ID NO: 7; and
   (b) evaluating said cell for β-galactosidase activity to determine whether said first and second proteins interact by said binding to each other, thereby complementing said first β-galactosidase fragment and said second β-galactosidase fragment.

2. The method according to claim 1, wherein said providing comprises introducing nucleic acids encoding said first and second fusion proteins into said cell.

3. The method according to claim 2, wherein said nucleic acids are introduced into said cell sequentially.

4. The method according to claim 2, wherein said nucleic acids are introduced into said cell simultaneously.

5. The method according to claim 1, wherein said method further comprises contacting said cell with a candidate interaction modulatory agent prior to said evaluating.

6. The method according to claim 1, wherein said evaluating comprises comparing observed β-galactosidase activity to said known level of β-galactosidase activity.

7. The method according to claim 1, wherein said variant minimal N-terminal β-galactosidase peptide comprises a point mutation between amino acids 29 to 41 that is a substitution.

8. The method according to claim 1, wherein said variant minimal N-terminal β-galactosidase peptide comprises a deletion between amino acids 29 to 41.

9. The method according to claim 1, wherein said point mutation, insertion or deletion occurs between residues 31 and 41.

10. The method according to claim 1, wherein said interaction occurs at an intracellular location.

11. The method according to claim 1, wherein said interaction occurs at a plasma-membrane location.

12. The method according to claim 1 wherein said variant minimal N-terminal β-galactosidase peptide has a sequence selected from the group consisting of SEQ ID NO: 1, SEQ ID NO: 2, SEQ ID NO: 3, SEQ ID NO: 4, and SEQ ID NO: 5.

13. The method according to claim 1 wherein the first protein and second protein are in a membrane of said cell.

* * * * *

UNITED STATES PATENT AND TRADEMARK OFFICE
CERTIFICATE OF CORRECTION

PATENT NO. : 8,541,175 B2  Page 1 of 1
APPLICATION NO. : 11/717579
DATED : September 24, 2013
INVENTOR(S) : Wehrman et al.

It is certified that error appears in the above-identified patent and that said Letters Patent is hereby corrected as shown below:

In the Specification under Column 1:

Please replace Column 1, line nos. 17-20 with:

--This invention was made with Government support under contract DAMD17-00-1-0442 awarded by the U.S. Army Medical Research Materiel Command and under contracts AG009521, AG020961, AG024987, and HD018179 awarded by the National Institutes of Health. The Government has certain rights in the invention.--

Signed and Sealed this
Twenty-ninth Day of September, 2015

Michelle K. Lee
*Director of the United States Patent and Trademark Office*